US011286461B2

(12) United States Patent
Visconti et al.

(10) Patent No.: US 11,286,461 B2
(45) Date of Patent: Mar. 29, 2022

(54) METHOD TO PREPARE SPERM

(71) Applicant: University of Massachusetts, Boston, MA (US)

(72) Inventors: Pablo E. Visconti, Amherst, MA (US); Felipe Navarrete, Hadley, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 16/089,862

(22) PCT Filed: Mar. 31, 2017

(86) PCT No.: PCT/US2017/025583
§ 371 (c)(1),
(2) Date: Sep. 28, 2018

(87) PCT Pub. No.: WO2017/173391
PCT Pub. Date: Oct. 5, 2017

(65) Prior Publication Data
US 2019/0119631 A1   Apr. 25, 2019

Related U.S. Application Data

(60) Provisional application No. 62/316,990, filed on Apr. 1, 2016.

(51) Int. Cl.
| *A61D 7/00* | (2006.01) |
| *A01N 1/02* | (2006.01) |
| *C12N 5/073* | (2010.01) |
| *A61K 48/00* | (2006.01) |
| *C12N 5/076* | (2010.01) |
| *C12N 15/00* | (2006.01) |
| *A61B 17/43* | (2006.01) |
| *A61B 17/435* | (2006.01) |
| *A61D 19/02* | (2006.01) |
| *A61D 19/04* | (2006.01) |

(52) U.S. Cl.
CPC ......... *C12N 5/0604* (2013.01); *A01N 1/0205* (2013.01); *A61B 17/43* (2013.01); *A61B 17/435* (2013.01); *A61D 19/02* (2013.01); *A61D 19/04* (2013.01); *A61K 48/00* (2013.01); *C12N 5/061* (2013.01); *C12N 15/00* (2013.01); *C12N 2501/998* (2013.01); *C12N 2501/999* (2013.01); *C12N 2517/10* (2013.01)

(58) Field of Classification Search
CPC ....... A61D 19/02; C12N 5/0604; C12N 5/061
See application file for complete search history.

(56) References Cited

U.S. PATENT DOCUMENTS

| 4,448,767 A | 5/1984 | Bryant |
| 4,999,283 A | 3/1991 | Zavos et al. |
| 5,250,417 A | 10/1993 | Feuchter |
| 5,575,914 A | 11/1996 | Jeyendran |

FOREIGN PATENT DOCUMENTS

| AU | 2017240224 B2 | 7/2020 |
| WO | WO-2010104882 A1 | 9/2010 |
| WO | WO-2017173391 A1 | 10/2017 |

OTHER PUBLICATIONS

Goldstein, Glenn A., 2008, U.S. 20080200548 A1.*
Vandevoort et al., 1995, Journal of Andrology, vol. 16, No. 4, p. 327-333.*
"International Application Serial No. PCT/US2017/025583, International Search Report dated Jun. 22, 2017", 2 pgs.
"International Application Serial No. PCT/US2017/025583, Written Opinion dated Jun. 22, 2017", 6 pgs.
Dasgupta, et al., "A possible role for Ca2+-ATPase in human sperm capacitation", Journal of Reproduction and Fertility, vol. 102, (1994), 107-116 pgs.
"Australian Application Serial No. 2017240224, First Examination Report dated Jul. 15, 2019", 3 pgs.
"European Application Serial No. 17776863.7, Extended European Search Report dated Aug. 28, 2019", 8 pgs.
Carrillo, Alberto J, "use of glucose- and phosphate-free media Setting: Hospital-based fertility clinic", Fertility and Sterility, (Jan. 1, 1998), XP55610743,, Retrieved from the Internet:URL oi.org 10.1016 50015-0282(97)00499-8, (Jan. 1, 1998), 6 pgs.
Goodson, Summer G., "Metabolic Substrates Exhibit Differential Effects on Functional Parameters of Mouse Sperm Capacitationl", Biology of Reproduction, vol. 87, No. 3, (Sep. 1, 2012), XP55612131, (Sep. 1, 2012), 15 pgs.
Navarrete, Felipe A, "Transient exposure to calcium ionophore enables in vitro fertilization in sterile mouse models", Scientific Reports, vol. 6, No. 1, (Sep. 15, 2016) XP55613936, (Sep. 15, 2016), 9 pgs.
Tateno, H, "Ca2+ ionophore A23187 can make mouse spermatozoa capable of fertilizing in vitro without activation of cAMP-dependent phosphorylation pathways", PNAS, vol. 110, No. 46, (Oct. 15, 2013), XP55610752,, (Oct. 15, 2013), 18543-18548.
"Canadian Application Serial No. 3,019,523, Office Action dated Sep. 30, 2019", 4 pgs.
"European Application Serial No. 17776863.7, Response filed Mar. 19, 2020 to Extended European Search Report dated Aug. 28, 2019", 11 pgs.
"Australian Application Serial No. 2017240224, Response filed Apr. 1, 2020 to First Examination Report dated Jul. 15, 2019", 12 pgs.
"Australian Application Serial No. 2017240224, Response filed Jun. 18, 2020 to Subsequent Examiners Report dated Apr. 2, 2020", 11 pgs.

(Continued)

*Primary Examiner* — Shin Lin Chen
(74) *Attorney, Agent, or Firm* — Schwegman Lundberg & Woessner, P.A.

(57) ABSTRACT

Methods for improving the functionality and/or fertility of sperm, for example, by enhancing motility and/or extending the lifespan of sperm by subjecting the isolated sperm to a starvation protocol and/or ionophore are provided. Such methods may be used in, for example, artificial insemination to reduce the number of sperm needed for insemination and to improve conception rates.

7 Claims, 23 Drawing Sheets

(56) References Cited

OTHER PUBLICATIONS

"Australian Application Serial No. 2017240224, Subsequent Examiners Report dated Apr. 2, 2020", 3 pgs.
"Canadian Application Serial No. 3,019,523, Response filed Mar. 30, 2020 to Office Action dated Sep. 30, 2019", 13 pgs.
"European Application Serial No. 17776863.7, Communication Pursuant to Article 94(3) EPC dated May 13, 2020", 6 pgs.
"European Application Serial No. 17776863.7, Communication Pursuant to Article 94(3) EPC dated Sep. 23, 2020", 6 pgs.
"European Application Serial No. 17776863.7, Response filed Sep. 4, 2020 to Communication Pursuant to Article 94(3) EPC dated May 13, 2020", 5 pgs.
"European Application Serial No. 17776863.7, Response filed Dec. 22, 2020 to Communication Pursuant to Article 94(3) EPC dated Sep. 23, 2020", 5 pgs.
"Canadian Application Serial No. 3,019,523, Office Action dated Oct. 21, 2020", 4 pgs.
"Canadian Application Serial No. 3,019,523, Response filed Apr. 14, 2021 to Office Action dated Oct. 21, 2020", 11 pgs.
"European Application Serial No. 17776863.7, Summons to Attend Oral Proceedings dated Feb. 25, 2021", 6 pgs.

* cited by examiner

[APPEARANCE OF THE VAGINA IN PROESTRUS]

MATE WITH VASECTOMIZED MALE

[VAGINAL PLUG]

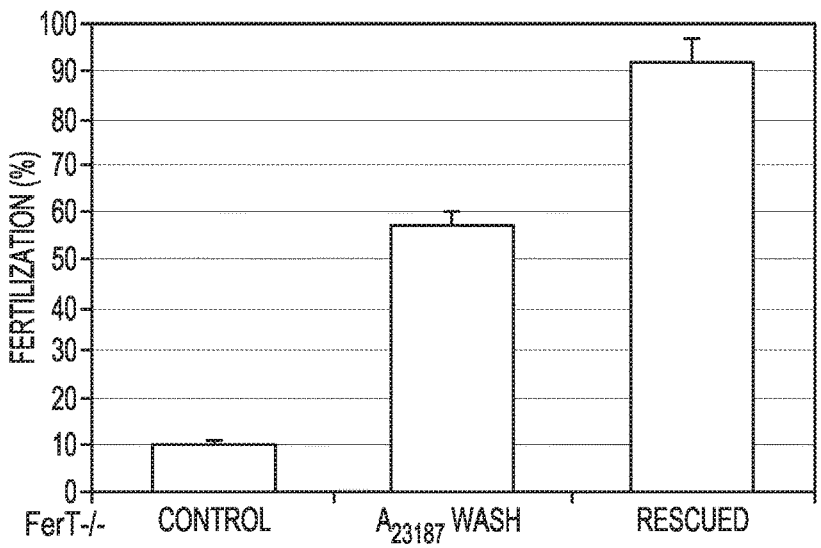
FIG. 12A
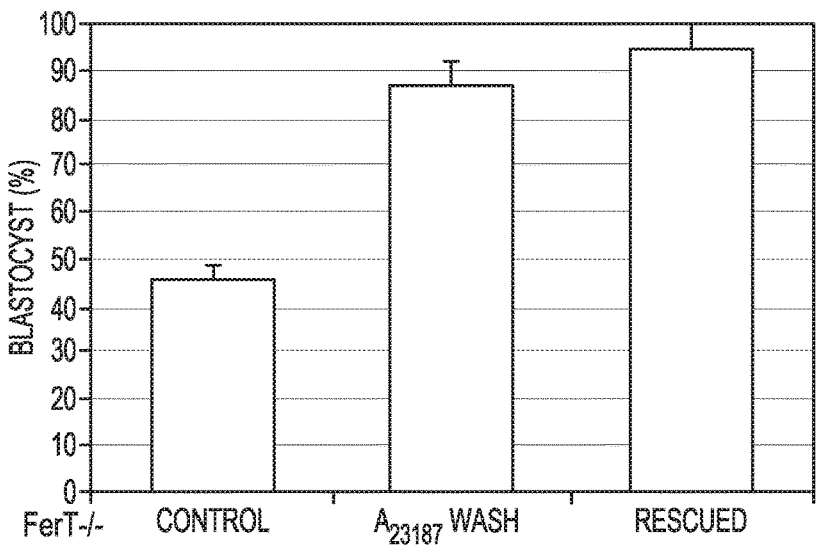
FIG. 12B
| TREATMENT | STRAIN/ GEOTYPE | CD-1 OOCYTES # | CLEAVAGE (%) | BLASTOCYST (%) | TOTAL (%) BLASTOCYST |
|---|---|---|---|---|---|
| CONTROL | SJL/J | 129 | 87 (67) | 62 (61) | 48 |
| RESCUE | | 159 | 140 (90) | 135 (96) | 87 |
| CONTROL | AKITA | 209 | 164 (78) | 119 (73) | 56 |
| RESCUE | | 266 | 247 (93) | 229 (93) | 86 |
FIG. 12C

METHOD TO PREPARE SPERM

PRIORITY

This application is a U.S. National Stage Filing under 35 U.S.C. 371 from International Application No. PCT/US2017/025583, filed on Mar. 31, 2017, and published as WO 2017/173391, which claims the benefit of priority from U.S. Provisional Patent Application Ser. No. 62/316,990, filed on Apr. 1, 2016, which are herein incorporated in their entirety by reference.

GOVERNMENT GRANT SUPPORT

This invention was made with government support under HD038082 and HD044044 awarded by the National Institutes of Health. The government has certain rights in the invention.

BACKGROUND

Assisted reproductive technology (ART) includes such techniques as in vitro fertilization (IVF), artificial insemination (AI), intracytoplasmic sperm injection (ICSI) (other techniques using enucleated cells) multiple ovulation and embryo transfer (MOET) and ART (as well as other embryo transfer techniques), is used across the animal kingdom, including humans and other animals. ART methods are usually expensive, time consuming and marginally successful given the inherent fragility of gametes and embryos when outside of their natural environments. Furthermore, the use of ART within the animal breeding industry in a commercially feasible manner is additionally challenging due to the limited availability of genetically desirable gametes and zygotes. One way to lower the cost of ART and to improve its commercial feasibility is to increase the efficiency of the involved processes by improving the viability and overall quality of gametes, zygotes and embryos.

For example, in conventional AI, one problem limiting its commercial application in certain species is the need to use extremely high number of sperm cells per AI dose to ensure successful fertilization. Similarly, in IVF, the percentage of zygotes that develop into embryos remains frustratingly low; this high rate of loss significantly increases the cost of embryos and related services to end-users.

SUMMARY OF THE INVENTION

The invention is directed to a novel method of treating sperm for artificial reproductive techniques including in vitro fertilization, ICSI, and artificial insemination such as intrauterine insemination (IUI) and intravaginal insemination (IVI). Each species can benefit from this technology, for example, improvement of IVF, ICSI and artificial insemination for humans; IVF for horses; maintenance of live sperm in extenders for pigs; improvement of ART for mice genetic models; and for all species, improvement of embryonic development after fertilization. For example, benefits include significantly improved percentage of success fertilization and/or embryonic development in all species. Or, for example, such as horse IVF, the method is unique as IVF in this species has not been achieved.

The present invention is based on the surprising finding that reducing intracellular energy molecules including, but not limited to ATP, using a nutrient starvation protocol carried out on isolated sperm can increase sperm functionality and fertility rates, as well as embryo development to blastocysts rates and that those blastocysts when transferred to a female increased pregnancy rates. Also, we have the surprising finding that treatment with calcium ionophore, such as A23187, for a short time period, in addition to increasing sperm motility and fertilization rates, A23187 significantly increased embryo development rates to blastocysts (Scientific Reports 6, Article number: 33589 (2016)). Accordingly, one embodiment of the present invention comprises a method of treating sperm cells by exposing sperm cells to conditions of temporary starvation obtained by removing energy substrates (which include, but are not limited to, glycolytic substrates and Krebs cycle substrates such as glucose, fructose, pyruvate, lactate, citrate or a combination thereof from sperm surrounding media), exposing the sperm cells to an ionophore and/or combining these procedures in different (any) order.

One embodiment provides a method to increase sperm functionality comprising a) isolating sperm; b) removing, or not, some or all endogenous energy nutrients including, but not limited to, glycolytic substrates and Krebs cycle substrates such as glucose, fructose, pyruvate, lactate, citrate or a combination thereof; c) placing said sperm in a media with reduced or no added energy nutrients (as defined in b)) for a period of time dependent on the species under consideration; and d) after (b and c), adding an energy nutrient (which is any energy substrate including but not limited to glycolytic substrates and Krebs cycle substrates such as glucose, fructose, pyruvate, lactate, citrate or a combination thereof) to said media and sperm, so as to increase sperm functionality as compared to sperm cells that had not undergone energy nutrient starvation.

One embodiment provides a method to increase Artificial Insemination pregnancy rates comprising a) isolating sperm; b) removing, or not, some or all endogenous energy nutrients including but not limited to glycolytic substrates and Krebs cycle substrates such as glucose, fructose, pyruvate, lactate, citrate or a combination thereof; c) placing said sperm in a media without an energy nutrient (as defined in b)) for a period of time; d optionally adding an energy nutrient (which is any energy substrate including but not limited to glycolytic substrates and Krebs cycle substrates such as glucose, fructose, pyruvate, lactate, citrate or a combination thereof) to said media and sperm of b) and/or c); and e) using said sperm from b), c) and/or d) for intrauterine (IUI) or vaginal insemination (IVI).

Another embodiment provides a method to increase fertility in vitro comprising a) isolating sperm; b) removing, or not, some or all endogenous energy nutrients including, but not limited to, glycolytic substrates and Krebs cycle substrates such as glucose, fructose, pyruvate, lactate, citrate or a combination thereof; c) placing said sperm in a media without an energy nutrient (which is any energy substrate including, but not limited to, glycolytic substrates and Krebs cycle substrates such as glucose, fructose, pyruvate, lactate, citrate or a combination thereof) (for a period of time dependent on the species under consideration); d) adding an energy nutrient (as defined in b and c) to said media and sperm of b and/or c); and e) contacting said sperm with an ovum of the same species as the sperm, so as to increase fertility as compared to a method where sperm cells have not undergone energy nutrient starvation.

Another embodiment provides a method to increase fertility using intracellular sperm injection (ICSI) comprising a) isolating sperm; b) removing, or not, some or all endogenous energy nutrients including, but not limited to, glycolytic substrates and Krebs cycle substrates such as glucose, fructose, pyruvate, lactate, citrate or a combination thereof;

c) placing said sperm in a media without an energy nutrient (which is any energy substrate including, but not limited to, glycolytic substrates and Krebs cycle substrates, such as glucose, fructose, pyruvate, lactate, citrate or a combination thereof) (for a period of time dependent on the species under consideration); d) optionally adding an energy nutrient (defined in b and c) to said media and sperm of b); and e) injecting the sperm of b), c) or d) inside an ovum of the same species as the sperm, so as to increase fertility as compared to a method where sperm cells have not undergone energy nutrient starvation.

Another embodiment provides a method to increase embryo quality comprising a) isolating sperm; b) removing, or not, some or all endogenous energy nutrients including, but not limited to, glycolytic substrates and Krebs cycle substrates such as glucose, fructose, pyruvate, lactate, citrate or a combination thereof; c) placing said sperm in a media without an energy nutrient (which is any energy substrate including, but not limited to, glycolytic substrates and Krebs cycle substrates such as glucose, fructose, pyruvate, lactate, citrate or a combination thereof); d) adding an energy nutrient (defined as in b) and c)) to said media and sperm; e) contacting said sperm with an ovum of the same species as the sperm; and f) allowing said sperm and ovum to develop into a blastocyst, so as to increase embryo quality as compared to a method where sperm cells have not undergone energy nutrient starvation.

Another embodiment provides a method to increase embryo quality comprising a) isolating sperm; b) removing, or not, some or all endogenous energy nutrients including, but not limited to, glycolytic substrates and Krebs cycle substrates such as glucose, fructose, pyruvate, lactate, citrate or a combination thereof; c) placing said sperm in a media without an energy nutrient (e.g., metabolic nutrient as defined in b)); d) optionally adding an energy nutrient (as defined in b)) to said media and sperm of b); e) injecting the sperm of b), c) or d) inside an ovum of the same species as the sperm; and e) allowing said sperm and ovum to develop into a blastocyst, so as to increase embryo quality as compared to a method where sperm cells have not undergone energy nutrient starvation.

In one embodiment, removal of energy nutrients from biological fluids will be done by washing the sperm using centrifugation techniques with media lacking metabolic nutrients (including, but not limited to, glycolytic substrates and Krebs cycle substrates such as glucose, fructose, pyruvate, lactate, citrate or a combination thereof). Depending on the species, the centrifugation procedure includes one, two or more washes.

In one embodiment, removal of energy nutrients from biological fluids including epididymal and seminal fluid will be done by passing the sperm through materials such as gel filtration resins (e.g. Sephadex®) or ion-exchange resins (e.g. DOWEX, DEAE). These resins will be used with the goal of removing metabolic nutrients including, but not limited to, glycolytic substrates and Krebs cycle substrates such as glucose, fructose, pyruvate, lactate, citrate or a combination thereof from the said biological fluids.

In one embodiment, removal of energy nutrients will be done using density gradients lacking energy nutrients including but not limited to Percoll® gradients.

In one embodiment, the sperm are in an energy nutrient (as defined herein) absent environment (step b and/or c) for any period of time (such as from about 1 minute to several hours, including about 5 minutes, about 10 minutes, about 15 minutes, about 20 minutes, about 25 minutes, about 30 minutes, about 35 minutes, about 40 minutes, about 45 minutes, about 50 minutes, about 1 hour, about 1.5 hours, about 2 hours, about 3 hours, about 4 hours, about 5 hours and so on, including about 18-24 hours).

In one embodiment, the energy nutrient added to said media in step d) is any energy substrate including, but not limited to, glycolytic substrates and Krebs cycle substrates such as glucose, fructose, pyruvate, lactate, citrate or a combination thereof.

In one embodiment, no energy nutrient will be added back in d). Sperm will be used for any assisted reproductive technique while in starving media lacking metabolic nutrients.

In one embodiment, decrease of intracellular energy pools in the form of ATP or other energy molecules will be obtained using inhibitors of any of the enzymes of glycolysis, Krebs cycle or mitochondria oxidative phosphorylation. In this embodiment, said reagents can be used alone or in combination with the starving protocols described above.

In one embodiment, decrease of intracellular energy pools (e.g. ATP) will be induced by incubation of sperm in the absence of divalent cations including, but not limited, to calcium and magnesium. In the absence of these cations, there is an influx of sodium ions towards the intracellular sperm compartments. To eliminate this excess of sodium, the sperm use high levels of ATP and reduce the total amount of ATP. Elimination of divalent cations can be done by eliminating them from biological fluids such as seminal fluid, by not adding the divalent cations to the incubation media, and/or by adding divalent cation chelators including, but not limited to, EDTA and EGTA. Elimination of divalent cations for assisted reproductive techniques including, but not limited to, IVF, ICSI, IUI and IVI, can be done alone or in combination with the starving protocol.

In one embodiment, the sperm is vertebrate, including mammalian, including, but not limited to human, murine, avian (poultry), bovine, porcine, ovine, camelids (e.g. alpaca) or equine.

In one embodiment, the sperm cells are exposed to an ionophore, such as a calcium ionophore. This embodiment will be used alone or in combination to starving protocols.

One embodiment provides the use of sperm, prepared according to the methods described herein, with the purpose of producing genetically modified species (including, but not limited, to mouse) using techniques such as gene editing (e.g. TALEN, CRISPR/CAS) or any other transgenic, knock-out/in technology in eggs, zygotes and other embryonic stages, including early embryonic stages such as morula and blastocyst as well as post-implantation.

One embodiment provides the use of sperm, prepared according to the methods described herein, as a vector to introduce DNA and/or RNA material in the egg by artificial insemination, in vitro fertilization or ICSI, with the purpose of producing genetically modified species (in some embodiments with the aid of techniques such as gene editing (e.g. TALEN, CRISPR/CAS) or any other transgenic, knock-out/in technology in eggs, zygotes and other embryonic stages, including early embryonic stages such as morula and blastocyst as well as post-implantation).

Thus, the invention provides a method for improving the functionality and/or fertilizing capability of sperm cells by subjecting them to reduced levels of intracellular energy in the form of ATP or other energy substrates. This decrease in ATP will be produced by a period of starvation, use of inhibitors of glycolytic, Krebs cycle, or oxidative phosphorylation, by incubation of sperm in media without divalent cations (achieved by elimination of divalent cations from incubation media, by addition of divalent cation chelators (including EDTA or EGTA), or by combination of these procedures), or by a combination of the said methodologies. The invention further comprises treating sperm cells with or without an ionophore, such as a calcium ionophore, optionally in combination with any of the methods described herein with the purpose of improving embryo development and pregnancy rates.

One embodiment provides a new Sperm Conditioning Medical Device, which can be assembled as a commercially available kit to improve Assisted Reproductive Technology (ART). The general translational objective of the invention is to generate a new ART technology to be applied in IVF, ICSI and AI in humans, as well as in the biomedical research industry of animal models for human diseases, and in the breeding industry. In particular, disclosed herein are sperm media conditions, particularly for the use in human sperm, as well as a sperm conditioning device that will allow for sperm treatment, and for changes in the sperm-containing suspension without the use of centrifugation. This new method/device has the potential of replacing current standard media and of revolutionizing ART practices worldwide. Specifically, a sperm-compatible, plastic column of approximately 2-5"×0.5" (L×W), and 10-ml total capacity is packaged with a gel filtration slurry such as Sephadex® G-15 or Sephadex G-25 which will allow for separation of the sperm cell fraction (larger size) from the low molecular weight components present in seminal fluid (or a sperm sample from other sources). The base of the column can be provided with a porous lining of either glass wool or a filtering membrane; this will be optional and/or depending on sperm species. As an alternative, a dialysis-based device from proper material and of appropriate pore size can be used. As another alternative, ion-exchange resins including, but not limited to, DOWEX, can be used instead of gel filtration. These known sperm medium components, of a much smaller MW, play a role metabolically in sperm motility and fertilizing capacity. In a first step, the sperm sample will be passed through the device, in which the slurry of Sephadex® G-15 or Sephadex G-25 is free of those components, labeled as Solution A. After a 45-60 min incubation, the sperm will be recovered in Solution B, which does contain those metabolically components. This metabolic switch allows for a highly competent sperm sample, with an increased motility and fertilizing capacity, and significantly improved pregnancy rates and potential for healthier embryo development.

In one embodiment, a kit is adapted to the needs of each species. Such kits can include generation of kits for better sperm conservation in extenders; kits for artificial insemination in all animal species including humans; kits for in vitro fertilization; kits for ICSI; and kits for treating sperm produced in vitro from stem cells.

BRIEF DESCRIPTION OF THE DRAWINGS

FIGS. 12A-12C. Starved plus rescue treatment improves fertilization rates and embryo development from sub-fertile strains. A. Fertilization rate of FerTDR/DR sperm incubated under control, transient exposure to A23187 CA2+ ionophore, or starved plus rescued protocols. Data represents average±SEM (n=6). B. Embryo development rates. Percentage of blastocysts obtained from two-cell embryos under the same conditions described in A. C. Fertilization and embryo development rates of Akita and SJL/J mice strains. Sperm were treated in control or starved plus rescued condition. The table indicates the number of oocytes used in 4 independent experiments, together with the number of cells that reach two-cell stage with the respective percentage. Two-cell embryos were transferred to KSOM media and further incubated for 3.5 days. The number of blastocysts obtained with the respective percentage of blastocysts from two-cell embryo is given. Finally, the last column represents the effectiveness of each treatment given by the percentage of blastocysts from the initial number of oocytes used in the assays.

DETAILED DESCRIPTION OF THE INVENTION

Definitions

Figure 1:
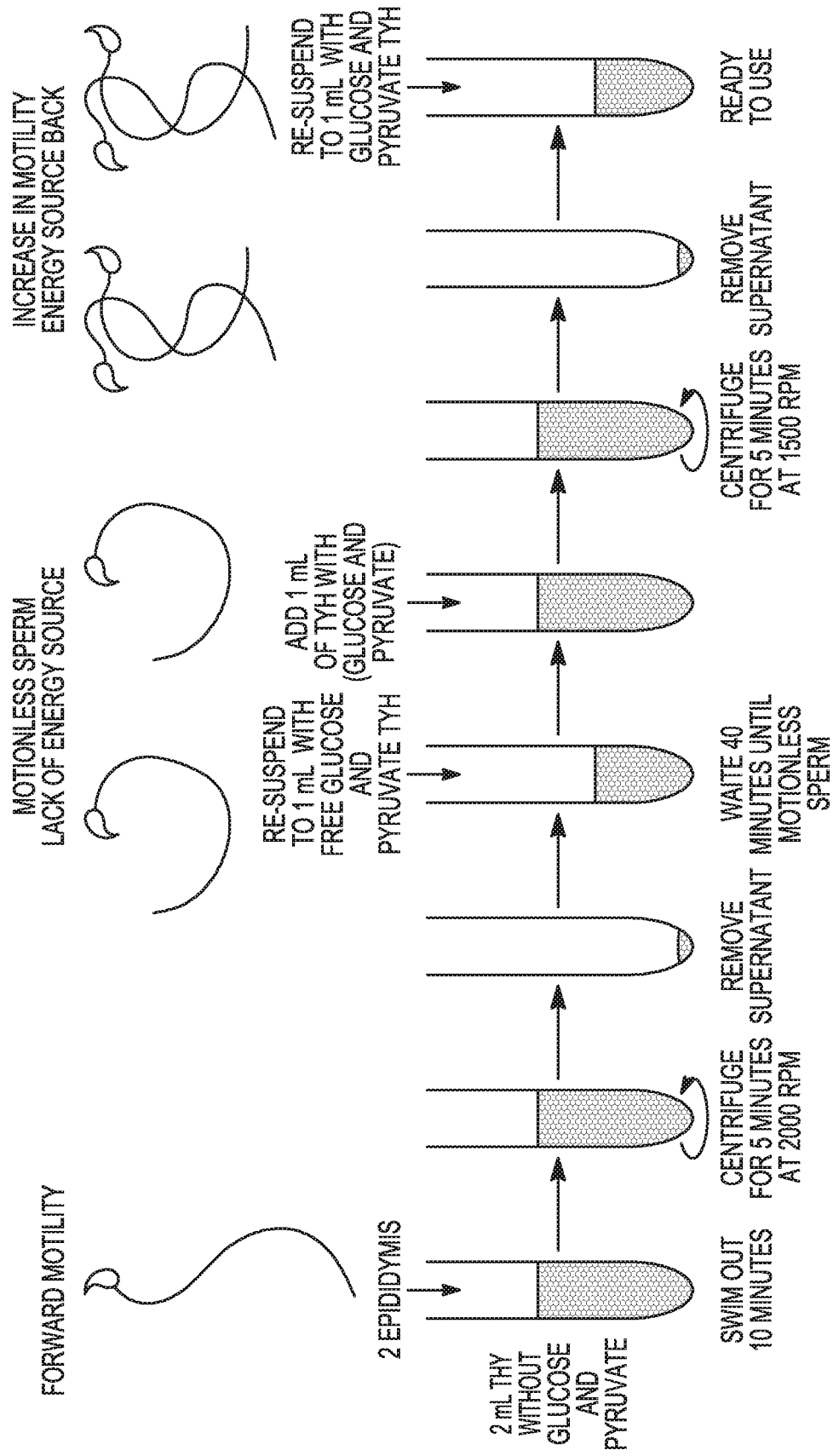
FIG. 1 depicts a motility assay.

In describing and claiming the invention, the following terminology will be used in accordance with the definitions set forth below. Unless defined otherwise, all technical and scientific terms used herein have the same meaning as commonly understood by one of ordinary skill in the art to which this invention belongs. Any methods and materials similar or equivalent to those described herein can be used in the practice or testing of the present invention. Specific and preferred values listed below for radicals, substituents, and ranges are for illustration only; they do not exclude other defined values or other values within defined ranges for the radicals and substituents.

As used herein, the articles "a" and "an" refer to one or to more than one, i.e., to at least one, of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The term "isolated" refers to a factor(s), cell or cells which are not associated with one or more factors, cells or one or more cellular components that are associated with the factor(s), cell or cells in vivo.

In relation to sperm, it should be understood that the terms "activity" and/or "function" encompass physiological processes such as, for example, sperm motility, sperm tropism (namely, the tendency of sperm to move towards or away from certain stimuli), capacitation (understood as the gaining of the ability to fertilize) and fertilizing ability. The terms "activity" and/or "function" may further include processes which occur prior to and during fertilization and/or interaction with the egg (or membranes/layers thereof)—such processes may include, for example sperm capacitation and acrosomal activity.

With regard to sperm motility, one of skill will appreciate that the term "motility" not only relates to general movement, but may be applied to other aspects of motility such as, for example, the speed of movement of a sperm cell and/or any increase or decrease in the proportion of moving sperm cells in any given population. It also applies to a specialized type of motility known as "Hyperactive motility or hyperactivation" which encompass changes in the symmetry of the sperm flagellum movement as well as in the force generated by such movement. As such, the PDEIs described herein may be used not only to increase sperm motility, but also to increase the speed of movement of a sperm cell, the changes in symmetry of the flagella, the changes in the force generated by movement and/or the proportion of moving and hyperactive cells in any given population of sperm.

The terms "comprises," "comprising," and the like can have the meaning ascribed to them in U.S. Patent Law and can mean "includes," "including" and the like. As used herein, "including" or "includes" or the like means including, without limitation.

Sperm

Sperm cell quality may refer to any one or a combination of the various attributes of sperm cells previously mentioned or further mentioned herein, such as, for example, viability, motility, functionality, stimulation, and preservation of the sperm, or fertility rates, insemination rates, or fertilization rates corresponding to the sperm (such as in the fertility of the sperm). Sperm cell characteristic may refer to any one or a combination of various biological, chemical, physical, physiological, or functional attributes of one or more sperm cells, such as chromosome bearing attributes of the cell, or in some embodiments may refer to sperm cell quality as previously described.

Sperm Sample Collection

The sperm sample may be a freshly collected sample from a source animal, such as bovine, equine, porcine, murine, human, or other vertebrate source including mammals, or a thawed, previously cryopreserved sample. Moreover, the sample may be a single ejaculate, multiple pooled ejaculates from the same mammal, or multiple pooled ejaculates from two or more animals. It can also be directly collected from any section of the male reproductive tract including testicular sperm, and sperm obtained from caput, corpus or cauda epididymis.

Various collection methods are known and include the gloved-hand method, use of an artificial vagina, and electro-ejaculation. The sperm are preferably collected or quickly transferred into an insulated container to avoid a rapid temperature change from physiological temperatures (typically about 35° C. to about 39° C.). The ejaculate typically contains about 0.5 to 15 billion sperm per milliliter, depending upon the species and particular animal. However, the number of sperm could be reduced because of subfertile or infertile phenotypes. In some cases, the sperm are directly taken from testicular or epididymal tissue using different methodologies such as puncture of the testis or epididymis using surgical procedures or removing the testis or epididymis and collecting the sperm in surrounding media.

Regardless of the method of collection, an aliquot may be drawn from the sperm sample and evaluated for various characteristics, such as for example, sperm concentration, sperm motility, sperm progressive motility, sample pH, sperm membrane integrity, and sperm morphology. This data may be obtained by examination of the sperm using, for example, the Hamilton-Thorn Motility Analyzer (IVOS), according to standard and well known procedures (see, for example, Farrell et al. Theriogenology (1998) 49(4): 871-9; and U.S. Pat. Nos. 4,896,966 and 4,896,967).

Dilution/Media

The sperm sample may be combined with a buffer (in the form of a solid or solution) to form a sperm suspension. Among other things, the buffer may enhance sperm viability by buffering the suspension against significant changes in pH or osmotic pressure. Generally, a buffer is non-toxic to the cells and is compatible with the dye used to stain the cells. Exemplary buffers include phosphates, diphosphates, citrates, acetates, lactates, and combinations thereof. Examples of such buffers include TRIS, TCA, TEST, bicarbonate/$CO_2$, sodium citrate, HEPES, TL, TES, citric acid monohydrate, HEPEST (Gradipore, St. Louis, Mo.), PBS (Johnson et al., Gamete Research, 17:203-212 (1987)), and Dulbecco's PBS (Invitrogen Corp., Carlsbad, Calif.).

One or more buffers may be combined together or with additives to form a buffered solution, and the buffered solution combined with the sperm sample to form a sperm suspension.

In addition to a buffer, the sperm suspension may also contain a range of additives to enhance sperm viability or motility. Exemplary additives include energy sources, protein sources, antibiotics, and compositions which regulate oxidation/reduction reactions intracellularly and/or extracellularly. One or more of these additives may be introduced into the buffer or buffered solution before the formation of the sperm suspension or, alternatively, may be separately introduced into the sperm suspension.

To minimize dilution shock, provide support to the cells, or disperse the cells throughout the suspension, a protein source may also be included in the buffer, buffered solution, or sperm suspension. Exemplary protein sources include egg yolk, egg yolk extract, milk (including heat homogenized and skim), milk extract, soy protein, soy protein extract, serum albumin, bovine serum albumin, human serum substitute supplement, and combinations thereof.

An antibiotic may be added to the sperm suspension in order to inhibit bacterial growth. Exemplary antibiotics include, for example, tylosin, gentamicin, lincomycin, spectinomycin, Linco-Spectin® (lincomycin hydrochloride-spectinomycin), penicillin, streptomycin, ticarcillin, or any combination thereof. The Certified Semen Services (CSS) and National Association of Animal Breeders (NAAB) have promulgated guidelines regarding the use of antibiotics with respect to sperm collection and use.

A composition which regulates oxidation/reduction reactions intracellularly and/or extracellularly may also be included in the sperm suspension. Such a composition may provide a protective effect to the sperm cells, such as for example by maintaining sperm viability or progressive motility. Examples of such a composition include, for example, pyruvate, vitamin K, lipoic acid, glutathione, flavins, quinones, superoxide dismutase (SOD), and SOD mimics. If included in the sperm suspension, such a composition may be present in a concentration sufficient to affect the protective effect without detrimentally affecting sperm health.

Nutrient Starvation Method

In the method disclosed herein, isolated sperm cells are placed in conditions absent energetic nutrient compounds. For example, most media that sperm cells are placed in contain glucose, lactate and/or pyruvate, which are energetic compounds. If such compounds are removed, the sperm cells are essentially starved because they lack energy sources. When each one is added back in singly, their individual role can be determined. It was determined that the sperm cells were not dead after being placed in a media free of energetic compounds. Rather, they just stopped swimming and appeared completely immotile. It was determined that glucose is more important than pyruvate as an energy source for mouse sperm. However, in other species, such as bovine, mitochondrial Krebs cycle and oxidative phosphorylation are more relevant.

| Nutrient(−) | Nutrient (+) |
| --- | --- |
| removing any type of carbohydrate/sugar/energy nutrient | adding any type of carbohydrate/sugar/energy nutrient yields increased motility after starvation/removal of sugar/energy nutrient |

Surprisingly, the sperm not only survive the starving process, but are very active. Even more surprisingly, they actually increase in activity—hyperactivated motility/hyperactivation. This is very good for fertilization. They also changed their motility pattern; in that they move very fast and the movement is more asymmetric. This led to increased IVF rates as compared to control (IVF without starvation of sperm cells prior to IVF) when sperm from a suboptimal strain of mice (CBL57, black six) were used.

For example, CD1 mice have a good fertilization rate to begin with, however, with the starvation method, the rate of zygotes going to blastocyst improved. In addition, the overall success of embryo development already good in CD1 mice improved; thereby showing an increase in embryo health. Although sperm of these mice are already good for IVF and embryo development, other mice strains have suboptimal fertilization and embryo development rates. Two cases assayed were C57BL/6, black six and Balb6. These mice naturally show poor rate for reproduction in vivo and in vitro and only 35% arrive to blastocyst, with approximately a 50% fertilization rate. However, with starvation method, both strains of mice show 90% and up to 100% go to blastocyst. This is a vast improvement and very surprising. It is believed that a sperm issue is the cause of balb6 and C57BL/6 mice not being good reproducers. With the sperm starvation protocol described herein, fertilization and embryo formation are greatly improved.

In the starvation protocol, isolated sperm are placed in an energy nutrient absent environment for a period (for example, until the sperm loose progressive motility) that could last from the starting point of the incubation in starving media to several hours depending on the species, including immediate contact up-to many seconds, minutes, hours or days. For example in mouse sperm the time to stop motility is between 30 min and 1 hour. In bull and human ejaculated sperm is between 3 and 5 hours. The time frame of incubation in starving media will depend on the species. The method can also be used to extend the life of sperm in extenders with limited amount of energy sources. In those cases, the embodiment contemplates suspending sperm treated or not with the starving procedure in media that contain zero or low concentrations of energy substrates.

The energy nutrient can be any agent/molecule that can provide energy or be used as energy by the sperm cells; this includes, but is not limited to, carbohydrates or sugar, including monosaccharides (such as fructose, glucose, galactose and mannose) and disaccharides (sucrose, lactose, maltose, and trehalose), as well as polysaccharides, galactose, oligosaccharides, polymers of sugar, glucose, pyruvate and combinations thereof. The energy nutrient can also be sodium lactate and lactic acid. Also, any other metabolizable molecule (e.g., any metabolite that has the potential to be converted in a source of energy including ATP, ADP, AMP, analogues of these compounds or compounds that could be converted in ATP, ADP or AMP) such as lipids, amino acids, nucleotides, etc.

Assisted Reproductive Technology (ART)

ART is the technology used to achieve pregnancy in procedures such as fertility medication, artificial insemination, in vitro fertilization and surrogacy. It is reproductive technology used primarily for infertility treatments, and is also known as fertility treatment. It mainly belongs to the field of reproductive endocrinology and infertility, and may also include intracytoplasmic sperm injection (ICSI) and cryopreservation. Some forms of ART are also used with regard to fertile couples for genetic reasons (pre-implantation genetic diagnosis).

The cost for fertility investigation and treatments can be great and many times insurance does not cover such procedures.

A) Artificial Insemination, IVF and ICSI

Artificial insemination in mice carried out with the starvation protocol described herein in which sperm were starved prior to use led to 55% of female pregnant, whereas control AI without starvation, led to only 10% of pregnancy. Moreover, litter size from pregnant females using starving sperm was on average 6 pups while pregnant females obtained with control sperm only deliver an average of 2 pups. Therefore, the protocol not only led to increased motility, but also increased fertility rates/ability to fertilize. Thus, the use of the sperm starvation protocol in humans can lead to the use of more artificial insemination procedures rather than IVF or ICSI.

IVF in humans is costly, easily about $15,000-$17,000 USD per try. In IVF, after fertilization, the cells are grown to the blastocyst stage and then implanted. Thus, not only fertilization and fertilization rates are important, but also rates of cells that continue on to blastocyst are important (improve embryo quality). The sperm cell starvation protocol described herein leads to an increase in both.

For Intracellular sperm injection (ICSI), it does not matter if the sperm are not motile. Thus, one would believe that a starvation protocol which leads to increased motility would not be needed. Surprisingly, in addition to fertility rates, embryo quality increased with the starvation protocol after conducting ICSI in bovine eggs. This improvement in bovine is very relevant because this species is known to be resilient to ICSI treatment. Maximum blastocyst formation using ICSI in bovines has been reported by many laboratories to be not more than 5%. Using the starving protocol, sperm injected using ICSI technology achieved 50% of cleavage (two cells).

In conclusion, the sperm cell starvation protocol is a method that improves in vitro fertilization, embryo quality, and artificial insemination.

B) Uses In Vitro in Infertility Clinics

Procedures used in infertility clinics to prepare human sperm samples for either in vitro fertilization, ICSI or intrauterine insemination can involve the starvation protocol described herein to prepare sperm samples prior to their use.

C) Agricultural Applications

The present invention is applicable to stimulating fertilizing ability of sperm in domestic animals. In many agriculturally important species (e.g., cattle, pigs, sheep) artificial insemination using either fresh or frozen/thawed semen samples is used to establish pregnancies. This is particularly important in controlled breeding programs where it is commercially advantageous for farmers to have specific genetically-determined traits introduced into their stock. Use of the methods described herein will result in improved pregnancy rates. Mammalian sperm are frequently damaged by freezing and thawing and results in lower fertility. By improving the performance of the viable sperm, the starvation protocol for sperm preparation used for insemination may promote a higher pregnancy rate per estrus cycle, reducing the number of cycles required to ensure conception and hence reducing the overall cost of artificial insemination. At the same time, semen from animals with highly desirable traits could be used to inseminate more females because fewer cycles would be needed to ensure conception in any one female.

D) Exotic Animals.

In zoos all over the world, reproduction of exotic species in captivity or in the wild is a relevant goal. The methods described herein including starving can be used to improve artificial insemination, IVF or ICSI in exotic species. In addition to those animals maintained captive in a zoo, conservation programs aim to improve reproduction in animals that are close to extinction in the wild. The methods described herein can be used for this purpose.

The following examples are intended to further illustrate embodiments of the invention and are not intended to limit the scope of the invention in any way.

EXAMPLES

Example I: Starvation Protocol

Materials

Males CD1 male 3-8 months old (or retired breeder) or C57BL6 mice; Females CD1 or C57BL6 6-8 weeks old; Hormones PMSG (G4877) y hCG (C1063); Filter (Sterivex 0.2 μm Millipore); Syringe (10 ml to filter media and 1 ml to inject hormones); BSA (Sharlip et al.), TL-Hepes Medium; TYH Standard; TYH Standard Free (Glucose and Pyruvate free); BSA (Sigma); 50 ml Falcon tubes; 15 ml Falcon tubes; 2 ml Falcon Tubes; 2 ml dishes; Tissue Culture dish 35×10 mm (Falcon ref 353001); Glass microcapilar (pipette); Aspirator tube; light mineral oil Fetus Bovine Serum (Atlanta Biologicals cat# S11150H); KSOM ((cat# MR-106-D))

Methods

Motility Assay (FIG. 1)
1. Sacrifice male mouse via dislocation or $CO_2$ chamber.
2. Open the abdomen with fine scissors. Begin from the pelvic area and make a V shape to see all the organs
3. Look for the testis (white pale balls) and follow the seminiferous tubules until you find the cauda of the epididymis (looks like a small brain).
4. Take the cauda epididymis and make three or four incisions until you see white fluid coming out.
5. Put cut 1 epididymis in 2 ml modified TYH-Hepes media (Free of glucose and Pyruvate) pH 7.2 to 7.4.
6. Leave the sperm to swim out of the tissue for 10 to 15 minutes.
7. Then take the 2 ml swim out and centrifuge for 5 minutes at 2000 RPM or subject the sperm to the device disclosed herein (with or without centrifugation).
8. Take the supernatant up to 300 ul or 500 ul.
9. Re-suspend up to 1 ml, including 2 ml, with modified TYH-Hepes (Glucose and Pyruvate Free)
10. Wait about 30-40 minutes until sperm stop moving
11. Add 1 ml of TYH supplemented with glucose 5 mM and pyruvate 800 uM.
12. Centrifuge for 5 minutes at 1500 RPM.
13. Take the supernatant up to 500 ul.
14. Re-suspend up to 1 ml of TYH supplemented with glucose 5 mM and pyruvate 800 uM.
15. Take 100 ul of the swim out and add it to capacitation media (TYH supplemented with 15 mM $HCO_3^-$ and 5 mg/ml serum albumin) with a final volume of 400 ul.
16. Wait about 60 minutes until sperm is fully capacitated (time can adjusted for species).
17. Check motility with CASA system.

Results/Discussion

Proof of principle has been conducted using mouse sperm. This can be extrapolated to other species including farm animals and humans.

Example II—In Vitro Fertilization/Starving Protocol Methods

Day 1:
Inject females with 5 IU (100 μl) of PMSG at 9-10 p.m. (hormones were prepared and diluted in sterilized PBS and keep to −20° C.).

Day 3:
Inject females with 5 IU (100 μl) of hCG at 9-10 p.m. (48 h after PMSG).

Figure 2:
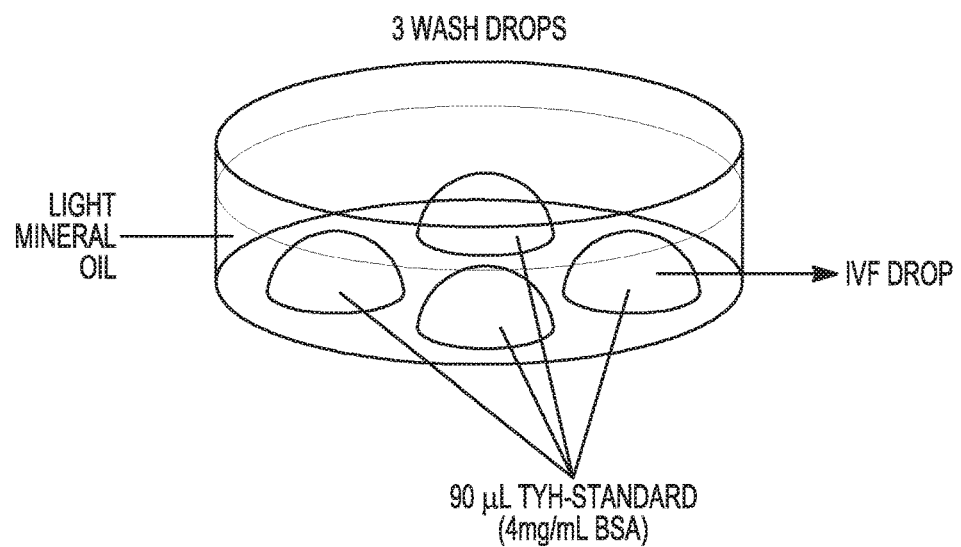
FIG. 2 depicts a prepared tissue culture dish for the IVF experiment.

Day Before IVF
Media:
5 ml TYH-Standard (4 mg/ml BSA) IVF at 37° C., 5% $CO_2$.
8 ml TYH-free glucose and pyruvate (4 mg/ml BSA) for sperm swim out at 37° C., 5% $CO_2$.
TL-HEPES supplemented with 5% Fetus Bovine Serum prepare the same of the IVF For Oocytes:
Prepare Tissue Culture dish 35×10 mm with 90 μl of media TYH-Standard (4 mg/ml BSA) IVF at 37° C., 5% $CO_2$. See FIG. 2 for further details.
Put different plates into incubator at 37° C., 5% $CO_2$.

For Oviducts:
Prepare Tissue Culture dish 35×10 mm with 90 μl of media TYH-Standard (4 mg/ml BSA) IVF at 37° C., 5% $CO_2$.
Put different plates into incubator at 37° C., 5% $CO_2$.

For Sperm:
Prepare 2 ml tube of TYH (Free of glucose and pyruvate for sperm swimming out)
Put tube into incubator at 37° C., 5% $CO_2$.

Figure 3:
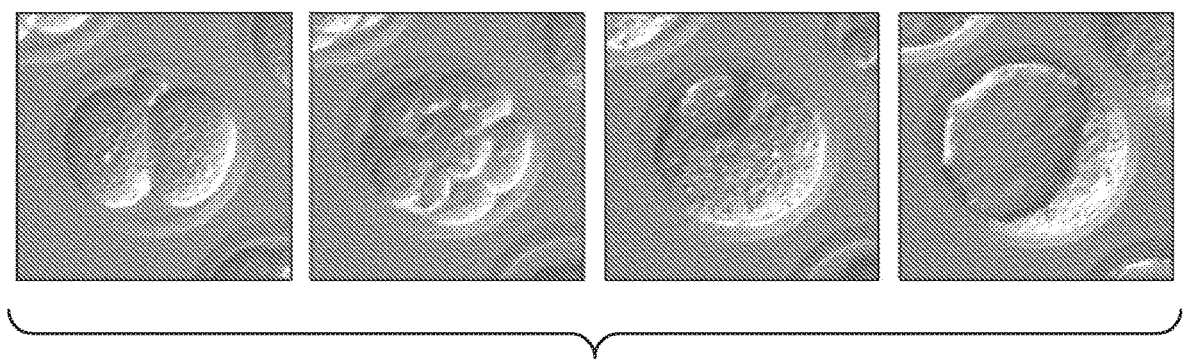
FIG. 3 depict images of embryos from two cells to blastocyst stage

Day 4:
9:30 Prepare TL Hepes
  Prepare TL-HEPES supplemented with 5% Fetus Bovine Serum
For oviducts:
  Prepare dish plate with 2 ml of TL-HEPES supplemented with 5% Fetus Bovine Serum (one to wash, and other to get the cumulus-oocyte complex).
10 a.m. Sperm collection
  Sacrifice male. Sperm cell from the cauda epididymes are spilt and allowed to swim out in 2 ml TYH-free glucose and pyruvate and standard TYH control medium for 10 min in 2 ml tube. Place the tube in at 37° C., 5% $CO_2$ incubator for 10 min.
  After 10 min take the 2 ml swim out and centrifuge for 5 minutes at 2000 RPM.
  Take the supernatant up to about 300 ul or 500 ul.
  Re-suspend up to 2 ml with TYH (Glucose and Pyruvate Free) or standard TYH control at 37° C., 5% $CO_2$
  Centrifuge for 5 minutes at 1500 RPM
  Take the supernatant up to 300 ul or 500 ul.
  Re-suspend up to 1 ml with TYH (Glucose and Pyruvate Free) or standard TYH control at 37° C., 5% $CO_2$
  Wait until sperm stop moving around 1 hour
  Add 1 ml of TYH-Standard with glucose and pyruvate at 37° C., 5% $CO_2$.
  Centrifuge for 5 minutes at 1500 RPM
  Take the supernatant up to 300 ul or 500 ul.
  Re-suspend up to 500 ul or 1 ml with TYH standard with glucose and pyruvate at 37° C., 5% $CO_2$
  Ready for insemination
10:30-11 a.m. Egg collection while sperm stop moving
  Sacrifice females super ovulated 13 to 14 hours after hCG administration.
  Remove oviducts and place in 1 ml TL-HEPES (5% FBS) medium in dish plate to rinse of blood and loose tissue.
  Open the oviducts with thin tweezers, and release the cumulus
  Using a fine-bore pipette transfer cumulus to a clean 2 ml TL-HEPES (5% FBS) dish.
  Transfer cumulus to a clean dish with 3 ml TYH standard at 37° C., 5% $CO_2$. Hepes inhibits IVF so make sure wash off the hepes very well before you place the cumulus in the IVF drop.
  Transfer cumulus to IVF drop leave at 37° C., 5% $CO_2$.
  Ready to be inseminated
11 a.m. Fertilization
  Inseminate using 20 μl of sperm capacitated. Co-incubate oocytes and sperm at 37° C., 5% $CO_2$ for 4 h, and then wash sperm of oocytes by transferring two times the oocytes into drop 1 and 2 with TYH-Standard with glucose and pyruvate (4 mg/ml BSA) using a fine-bore pipette.
  After washing, place oocytes in post-fertilization drop 3 and incubate up to 24 h at 37° C., 5% $CO_2$.
Day 5:
  12:30 a.m. to 2:00 pm Putative zygote evaluation:
  Check for two pronuclei or two embryo
  Follow embryo culture protocol
  Embryo Culture
  Following day after IVF Prepare dishes with KSOM medium drops (50 ul) covered with light mineral oil and put it in $CO_2$ incubator at 37 C for 1 hour before transferring 2 cell stage embryos.
  Transfer 2 cell embryos to KSOM medium (wash 2 times) make the same dish as the IVF, instead add 25 ul of KSOM medium.
  Transfer only 35 2-cell embryos per drop of KSOM culture drop
  This day follow the pseudo-pregnant female preparation chart.
  Wait 2.5 days until blastocyst formation; see FIG. 3.
  At blastocyst stage ready to transfer
Embryo Transfer and Pseudo-Pregnant Females

| DAY-0 | DAY-1 | DAY 2 | DAY 3.5 |
|---|---|---|---|
| IVF start 11 AM Finish 4 pm | Transfer 2 cell Embryos to KSOM (1 pm to 4 pm) Mate the females with vasectomized Males at 5 pm. Mice mate at midnight (day 0) | Check plugs at 9 am, and separate females with plug 12 pm (day1) | Do embryo transfer before noon in the 12 pm 2.5 day |

| Thursday Day-0 | Friday Day-1 | Saturday Day-2 | Sunday-Day3 | Monday 3.5 |
|---|---|---|---|---|
| IVF start 11 AM Finish 4 pm | Transfer 2 cell Embryos to KSOM (1 pm to 4 pm) | | Check for Morulas | Do embryo transfer at 6 to 12 am am in the morning |
| Recipients Females- | Mate the females with vasectomized Males at 5 pm. Mice mate at midnight 12 pm (day 0) | Check plugs at 9 am, and separate females with plug 12 pm (day1) | 12 pm (day 2) | 12 pm 2.5 day |

Embryo Transfer Procedures
1. Place a 15 μl drop of culture medium (KSOM already equilibrated at 37 C 5% $CO_2$) onto the lid of a 100 mm petri dish (Falcon 1029, or similar).
2. Load 12-20 blastocysts into the medium using a standard embryo-handling pipette. (Note: optimal number of embryos to transfer will vary depending upon mouse strain and manipulations embryos have received.)
3. Place the NSET device onto a P2 pipette that has been set to 1.8 μl. Recommended pipettes are the Pipette Rainin Classic PR2, 0.1-2 μl or Gilson Pipetman P2, 0.2-2 μl.
4. Press pipette plunger to first stop, lower tip of the NSET device into medium and slowly pull embryos into the tip. Remove NSET device tip from medium.
5. Carefully set pipette to 2.0 μl to create a small air bubble at NSET tip to help ensure embryos stay inside device tip during insertion into the mouse. Gently lay pipette with loaded tip aside (near cage) for use in step #9
6. Place the un-anesthetized recipient female on top of a cage with a wire rack, allowing the mouse to "grab" the cage bar surface with its forefeet. Grasp the midpoint of the tail using thumb and forefinger, and angle the tail upward while lightly pressing the base of the tail with the opposite edge of the hand.

7. Gently place smaller speculum into mouse's vagina, and then remove. This will help open the vagina.
8. Place larger speculum into vagina. Using an adequate light source, shine the light into the speculum to visualize the cervix.
9. While holding the female mouse with one hand as described in step #6, carefully pick up the pipette and gently insert the NSET device tip into the large speculum and through the cervix. Once NSET device hub contacts speculum, expel embryos by pressing plunger completely.
10. Gently remove NSET device without releasing pipette plunger and remove speculum. Return mouse to cage. No post-procedure monitoring is required.

Artificial Insemination

Animals: Female mice (at least 8 weeks old); Male mice as sperm donors Sperm (C57BL6/J);
Male vasectomized mice (VASEX=vasectomized male)
Equipment: NSET device with specula; P-20 Rainin/Gilson pipette; 1 cc syringes, 26 gauge needles; Scissors, forceps; IVF Tissue culture dishes (Falcon Cat#353653); Microscope (s); Wire-topped cage

| Monday Day-0 | Tuesday Day-1 | Wed Day-2 | Thursday-Day3 | Friday 4 |
|---|---|---|---|---|
| PMSG Injection 5 IU 5:30 pm | NONE | hCG Injection 5 IU 5:00 pm | AI at 9:00 am Add 40 ul of sperm/female | |
| Recipients Females- | NONE | | Put super-ovulated females with the vasectomized males | Check plugs at 9 am, and separate females with plug |

Figure 4:
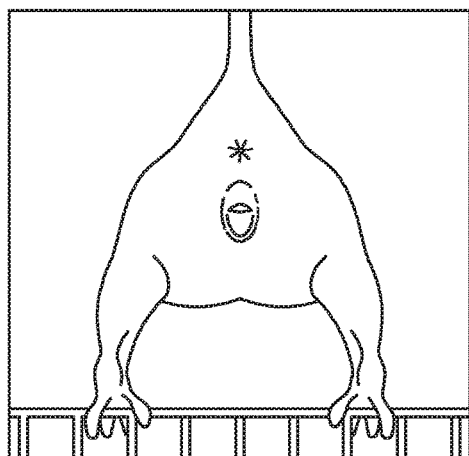
FIG. 4 depicts a mouse proestrus and with vaginal plug.
Figure 4:
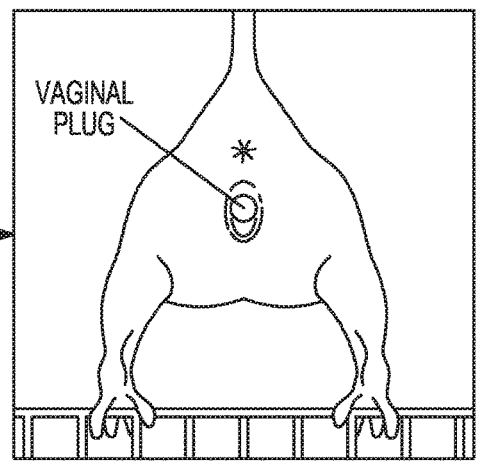

Sperm Preparation
1. Take one male Mice, sacrifice via dislocation or CO2 chamber.
2. Open the abdomen with fine scissors. Begin from the pelvic area and make a V shape so you can see all the organs
3. Look for the testis (white pale balls) and follow the seminiferous tubules until you find the cauda of the epididymis (looks like a small brain).
4. Take the cauda epididymis and make three or four incisions until you see white fluid coming out.
5. Take one epididymis for treatment and one for the control
6. Place epididymis in 2 ml modified TYH-Hepes media with 5% BSA (Free of glucose and Pyruvate) pH 7.2 to 7.4. Notice the control must have glucose and pyruvate.
7. Leave the sperm to swim out of the tissue for 10 to 15 minutes.
8. Then take the 2 ml swim out and centrifuge for 5 minutes at 2000 RPM.
9. Take the supernatant up to 300 ul.
10. Re-suspend up to 2 ml with modified TYH-Hepes media with 5% BSA (Glucose and Pyruvate Free)
11. Then take the 2 ml swim out and centrifuge for 5 minutes at 1500 RPM
12. Take the supernatant up to 300 ul.
13. Wait around 40 minutes until sperm stop moving
14. Ready to inseminate the female: At 9:00 am: Deliver sperm to the uterine horn using the NSET procedure.
   Place the NSET device onto a P-20 pipette that has been set to 20 pl.
   Press pipette plunger to first stop, lower tip into media at the edge of the sperm sample and slowly load sperm into the NSET device. Avoid clumps. Set aside pipette. Sperm at the edge of the sperm sample are
   Place the un-anesthetized recipient female on the top of a cage, allowing the mouse to "grab" the cage bar surface with its forefeet. Grasp the midpoint of the tail using thumb and forefinger, and angle the tail upward while lightly pressing the base of the tail.
   Place small speculum into vagina.
   While holding the female mouse with one hand as described above, carefully pick up the pipette and insert the NSET tip into the speculum, through the cervix and into the uterus. Once NSET hub contacts speculum, expel sperm by pressing plunger to the first stop.
   Repeat procedure to deliver a total sperm volume of 40 but wash NSET device with a TYH-Hepes media with 5% BSA (Free of glucose and Pyruvate) every time device goes into the uterus. This prevents contamination of Starved sperm with metabolic substrates present in the uterus
   Remove NSET device and speculum. No post-procedure monitoring is required.
15. Immediately pair the female with a VASEX male overnight. Copulatory activity seems to be required to obtain pups from this procedure but not for embryo fertilization.
2. Dissolve Mating Pairs Day 5:
a. Remove the female from the VASEX male cage.
b. Visually check for a copulation plug. The female is removed from the mating cage and transferred to the top of a wire-topped cage. Visual inspection and/or a blunt-end probe may be used to determine the presence of a vaginal plug (FIG. 4).

Results

Example III—Method for Treating Sperm with $Ca^{2+}$ Ionophores Alone and in Combination with Starvation to Improve Embryo Development Abstract Mammalian sperm acquire fertilizing capacity in the female tract in a process called capacitation. As part of capacitation, sperm undergo changes in their motility pattern (i.e., hyperactivate) and become prepared for an exocytotic acrosome reaction that is necessary for fertilization. At the molecular level, capacitation requires a fast activation of protein kinase A (PKA) which is followed by hyperpolarization of the sperm plasma membrane and an increase in intracellular $Ca^{2+}$. Genetic or pharmacological inhibition of these pathways results in loss of fertilizing ability both in vivo and in vitro. Recently, it was demonstrated that transient incubation of mouse sperm with the Ca2+ ionophore A23187 accelerated capacitation and rescued fertilizing capacity in sperm with inactivated PKA function (1). Based upon these results, it was believed that A23187 could be used to overcome defects in signaling pathways upstream of the increase in intracellular $Ca^{2+}$ required for capacitation. It is herein shown that a pulse of ionophore induces fertilizing capacity in sperm from infertile CatSper1 (sperm specific $Ca^{2+}$ channel), Adcy10 (soluble adenylyl cyclase sAC) and SLO3 (sperm-specific K+ channel) KO mice. In contrast, sperm from infertile mice lacking the $Ca^{2+}$ efflux pump PMACA4 (Plasma membrane $Ca^{2+}$-ATPase) were not rescued by ionophore. These results indicate that a transient increase in intracellular $Ca^{2+}$ can be used to overcome genetic infertility in mice and suggest this approach may prove adaptable to rescue male infertility of other species in which in vitro fertilization protocols are currently unsuccessful.

Introduction

While treating sperm with $Ca^{2+}$ ionophores is known ($Ca^{2+}$ ionophore A23187 can make mouse spermatozoa capable of fertilizing in vitro without activation of cAMP-dependent phosphorylation pathways). It was not appreciated that this treatment impacted embryo development. Further, $Ca^{2+}$ ionophore treatment (such as $Ca^{2+}$ ionophore A23187) has not been used in conjunction with starvation to improve fertility procedures.

In 1978, Steptoe and Edwards reported the birth of Louise Joy Brown, the first successful "Test-Tube" baby (2). A major step toward this achievement (3) occurred in the early 1950's, when Chang (4) and Austin (5) demonstrated independently that sperm have to be in the female reproductive tract for a period of time before acquiring fertilizing capacity, a phenomenon now known as sperm capacitation. Capacitation includes all post-ejaculation biochemical and physiological changes that render mammalian sperm able to fertilize (4, 5). As part of capacitation, sperm become prepared to undergo acrosomal exocytosis (6, 7) and undergo changes in their motility pattern (e.g. hyperactivation). Although the molecular basis of these physiological processes is not well understood, capacitation is associated with: 1) activation of a cAMP/protein kinase A (PKA) pathway (8, 9); 2) loss of cholesterol (10, 11) and other lipid modifications (12); 3) increase in intracellular pH (pHi) (13); 4) hyperpolarization of the sperm plasma membrane potential (14, 15, 16); 5) increase in intracellular $Ca^{2+}$ concentration $[Ca^{2+}]i$ (17); and 6) increase in protein tyrosine phosphorylation (9, 18). These pathways were first identified as playing a role in capacitation using compounds that stimulate or block the respective signaling processes. More recently, the essential role of cAMP, $Ca^{2+}$ and plasma membrane hyperpolarization was confirmed using KO genetic approaches (19, 20).

The role of cAMP in capacitation and fertilization was asserted using reagents such as cAMP agonists (dibutyryl cAMP, 8-BrcAMP) and antagonists of PKA-dependent pathways (e.g. H89, PKI, rpScAMP), as well as other conditions in which soluble adenylyl cyclase Adcy (10 21), the major source of cAMP in sperm, cannot be activated (e.g. $HCO_3^-$-free incubation media; addition of KH7, a specific sAC inhibitor) (for review see 7). The roles of cAMP were confirmed using KO genetic mouse models lacking either the PKA sperm-specific catalytic splicing variant Cα2, or sAC; these mice are sterile and their sperm cannot fertilize in vitro (22). It was demonstrated that hyperpolarizing changes in membrane potential are necessary and sufficient to prepare the sperm for a physiological acrosome reaction (23). Accordingly, sperm missing the sperm-specific $K^+$ channel SLO3 cannot hyperpolarize and are infertile (24, 25). Finally, $Ca^{2+}$ was shown to be essential for hyperactivation and the acrosome reaction by using $Ca^{2+}$-free incubation media with or without addition of chelating agents such as EGTA to decrease this ion concentration or using $Ca^{2+}$ ionophores such as A23187 to elevate it (1). Consistent with this, sperm-specific $Ca^{2+}$ channel complex CatSper KO mice are infertile, and their sperm are unable to hyperactivate.

Recently, it was found that addition of $Ca^{2+}$ ionophore A23187 produced a fast increase in intracellular $Ca^{2+}$ that was accompanied by complete loss of sperm motility (1). After A23187 removal, intracellular $Ca^{2+}$ levels dropped and sperm gain hyperactive motility (1). In addition to inducing hyperactivated motility, this $Ca^{2+}$ ionophore A23187 pulse enhanced fertilizing capacity. Interestingly, this $Ca^{2+}$ ionophore pulse supported capacitation in sperm incubated under non-capacitating conditions, and it induced hyperactivation and the capacity to fertilize in vitro even under conditions where cAMP-dependent pathways are blocked (1). These results suggested that A23187 could overcome defects in the signaling pathways upstream of the increase in intracellular $Ca^{2+}$ required for capacitation. This was tested using infertile genetic mouse models. Consistent with the hypothesis, a short A23187 pulse overcomes the infertile phenotypes of CatSper (19), sAC (22) and SLO3 KO sperm (25). The previous results suggested that subsequent washout of A23187, sperm intrinsic mechanisms involved in extruding $Ca^{2+}$ are necessary to induce hyperactivation and fertilizing capacity (1). Consistent with this hypothesis, sperm lacking the $Ca^{2+}$ efflux pump PMCA4, which mediates $Ca^{2+}$ extrusion (26), were not rescued by the ionophore treatment, suggesting that this ATPase is required downstream to remove excess intracellular $Ca^{2+}$.

Materials and Methods

Materials

Different materials and chemicals were purchased from different companies (codes between parenthesis represent the catalog number of the respective compound): Calcium Ionophore A23187 (C7522; dissolved in DMSO 2 mM stock), Bovine serum albumin (BSA, fatty acid-free) (A0281), Tween-20 (P7949), fish skin gelatin (G7765), Pregnant mare serum gonadotropin (G4877) and human chorionic gonadotropin (CG5), were purchased from Sigma (St. Louis, Mo.). Non-Surgical Embryo Transfer (NSET) Device was acquired from Paratechs (Billerica, Mass.). N-[2-[[3-(4-bromophenyl)-2-propen-1-yl]amino]ethyl]5-isoquinolinesulfonamide, and dihydrochloride H-89 (130964-39-5) were purchased from Cayman chemical (Ann Arbor, Mich.). Anti-phosphotyrosine (anti-PY) monoclonal antibody (clone4G10), embryo transfer light mineral oil (ES-005-C) and EmbryoMax® KSOM Medium (1×) w/ 1/2 Amino Acids (MR-106-D) were obtained from Millipore (Billerica, Mass.). Rabbit monoclonal anti-phosphoPKA substrates (anti-pPKAS) (clone100G7E), was purchased from Cell Signaling (Danvers, Mass.). Horseradish peroxidase-conjugated anti-mouse and anti-rabbit IgGs were purchased from Jackson ImmunoResearch Laboratories (West Grove, Pa.) and GE Life Sciences. Triton X-100 (161-0407), 30% Acrylamide and β-Mercaptoethanol was obtained from Biorad.

Animals

CD1 (Charles River Laboratories, Wilmington, Mass.) and C57BL/6 background mice, 7-18 wk of age, were used. Infertile KO mice genetic models (CatSper−/−, sAC−/− and SLO3−/−) were in C57BL/6 background; PMCA4−/− mice were in FVBN background. For CatSper embryo recipients, surrogate mothers were CD1 females, 8-12 wk of age. Animals were sacrificed in accordance with the Animal Care and Use Committee guidelines of UMass, Amherst. In experiments in which phosphorylation by PKA and tyrosine phosphorylation was investigated, CD1 and C57BL/6 male mice were used as indicated in the respective figure legend.

Media

Medium used for sperm capacitation and fertilization assays was Toyoda-Yokoyama-Hosi (standard TYH) medium. Containing 119.37 mM NaCl, 4.7 mM KCl, 1.71 mM $CaCl_2.2H_2O$, 1.2 mM $KH_2PO_4$, 1.2 mM $MgSO_4.7H_2O$, 25.1 mM $NaHCO_3$, 0.51 mM Na-pyruvate, 5.56 mM glucose, and 4 mg/mL bovine serum albumin (BSA), 10 μg/mL Gentamicin and phenol red 0.0006% at pH 7.4 when equilibrated with 5% $CO_2$. To analyze the role of capacitation in phosphorylation pathways an HEPES-modified TYH media was used. Media that does not support capacitation (Non-Cap) contained 20 mM HEPES instead of $HCO3-$ and does not contain BSA. For capacitating conditions HEPES-modified TYH was supplemented with 15 mM $HCO3^-$ and 4 mg/ml of BSA. $Ca^{2+}$ ionophore A23187 (Sigma Aldrich, location) was used at 20 μM in TYH or H-TYH. Non-capacitating H-TYH was prepared by replacing 25 mM $NaHCO_3$ with 20 mM Na-Hepes. Day before IVF add 4 mg/ml BSA.

Mouse Sperm Preparation for Western Blots

Cauda epididymal mouse sperm were placed in 1 ml Hepes-TYH media as stated in figure legend for each experiment. After 10 min incubation at 37° C., epididymides were removed, and the suspension adjusted with non-cap medium to a final concentration of $1-2 \times 10^7$ cells/ml. After dilution 1:4 (total 400 ul), sperm were incubated at 37° C. for 1 hour in conditions that support or not capacitation. For capacitation, media was supplemented with 15 mM $NaHCO_3$ and 4 mg/ml BSA. For A23187 treatment, 500 uL of the sperm suspension were taken from the initial swim out and supplemented with 20 μM A23187 for 10 minutes. Then, A23187 was washed off with 2 rounds of centrifugations 1-) 2000 RPMS and the 2-) 1500 RPMS for 5 min each. Sperm were re-suspended in free A23187 media. To evaluate the behavior of A23187 when PKA is inactivated, H89 was used at a concentration of 50 uM for all incubation periods including those used for washing A23187. Sperm proteins were then extracted for western blotting.

SDS-PAGE and Immunoblotting

Sperm were centrifuged, and washed in 1 ml of phosphate buffer solution (PBS), re-suspended in Laemmli sample buffer (63), and boiled for 4 min. Before Loading, 5% β-mercaptoethanol was added to the protein extracts and boiled for 3 min. Protein extracts equivalent to $1 \times 10^6$ sperm were loaded per line and subjected to SDS-PAGE an electro-transfer to PVDF membranes (Bio-Rad) at 250 mA for 60 min on ice. For anti pPKA substrates Western blots, membranes were blocked with 5% fat-free milk in TBS containing 0.1% Tween 20 (T-TBS). For anti-pY, membranes were blocked with 20% fish skin gelatin (54) in T-TBS. Antibodies were diluted in TBS containing 0.1% Tween-20 as follows: 1/10,000 for anti-PY (clone4G10), and 1/1000 for anti-pPKA (clone100G7E). Secondary antibodies were diluted 1/10,000 in T-TBS and developed using an enhanced chemiluminescence detection kit (ECLplus, Amersham, GE Healthcare) according to the manufacturer's instructions. When necessary, PVDF membranes were stripped at 65° C. for 15 min in 2% SDS, 0.74% β-mercaptoethanol, 62.5 mM Tris, pH 6.5, and washed six times for 5 min each in T-TBS.

Motility and IVF Sperm Ionophore Pre-Treatment

Sperm from CD-1, C57BL6 (K.O control), CatSper KO 19, SLO3 KO (56), Soluble Adenylyl Cyclase KO (20), and PMC4 KO (35) cauda epididymides were allowed to swim out in 1 mL of standard TYH for 10 minutes. Each swim out tube was split in two halves (500 ul each) and one half was incubated with 20 uM A23187 for 10 minutes. Then, the A23187 was washed by centrifugation as described above (2000 and 1500 RPMS×5 min), the remaining sperm were re-suspended in free A23187 TYH standard medium and capacitated for an addition 1 hour and 20 minutes before adding the sperm to the fertilization drop or for CASA analysis.

Sperm Motility Analysis

Sperm suspensions (25 μl) were loaded into one prewarmed chamber slide (depth, 100 μm) (Leja slide, Spectrum Technologies) and placed on a microscope stage at 37° C. Sperm movements were examined using the CEROS computer-assisted semen analysis (CASA) system (Hamilton Thorne Research, Beverly, Mass.). The default settings include the following: frames acquired: 90; frame rate: 60 Hz; minimum cell size: 4 pixels; static head size: 0.13-2.43; static head intensity: 0.10-1.52; static head elongation: 5-100. Sperm with hyper activated motility, defined as motility with high amplitude thrashing patterns and short distance of travel, were sorted using the criteria established by (64). The data was analyzed using the CASA nova software (64). At least 20 microscopy fields corresponding to a minimum of 200 sperm were analyzed in each experiment.

Video Recordings

Sperm suspensions (25 μl) were loaded into one prewarmed chamber slide (depth, 100 μm) (Leja slide, Spectrum Technologies). Videos were recorded for 15 seconds using an Andor Zyla microscope camera (Belfast, Northern Ireland) mounted on Nikon TE300 inverted microscope (Chiyoda, Tokyo, Japan) fitted with 10 and 20 times objective lenses. Sample temperatures were maintained at 37° C. using a Warm Stage (Frank E. Fryer scientific instruments, Carpentersville, Ill.).

Mouse Eggs Collection and IVF Assays

Metaphase II-arrested eggs were collected from 6-8 week-old super ovulated CD-1 female mice (Charles River Laboratories). Females were each injected with 5-10 IU equine chorionic gonadotropin and 5-10 IU human chorionic gonadotropin 48 h apart. The cumulus-oocyte complexes (COC's) were placed into a well with 500 μl of media (TYH standard medium) previously equilibrated in an incubator with 5% $CO_2$ at 37° C. Fertilization wells containing 20-30 eggs were inseminated with sperm (final concentration of $2.5 \times 10^6$ cells/ml) that had been incubated for 1 h and 20 min (in a medium supporting capacitation with or without calcium ionophore treatment A23187). After 4 h of insemination, eggs were washed and put in a fresh media. The eggs were evaluated 24 h post-insemination. To assess fertilization the three following criteria were considered: 1) the formation of the male and female pronuclei, 2) the emission of the second polar body, and 3) two cells stages.

Embryo Culture, Embryo Transfer and Mice Genotyping

Fertilized 2 cell embryos were cultured in KSOM media to blastocyst stage between 3.5 days wt and K.O between 3.8 to 4.1 days. Then they were transferred to 2.5 days post coitum (dpc) pseudo-pregnant CD-1 recipient females using the non-surgical uterine embryo transfer device (65). Pseudo-pregnant CD-1 recipient females were obtained by mating with vasectomized males one day after in vitro fertilization. Only females with a clear plug were chosen as embryo recipients; late morula and early stage blastocysts were chosen to be transferred. Routine genotyping was performed with total DNA from tail biopsy samples from weaning age pups as templates for PCR using genotyping primers for Catsper gene forward [5'-TAAGGACAGTGACCCCAAGG-3'] and reverse [5'-TAAGGACAGTGACCCCAAGG-3'] and for the reporter gene Lacz forward [5' TGATTAGCGCCGTGGCCTGATT-CATTC-3'] and reverse [5'-AGCATCATCCTCTG-CATGGTCAGGTC-3'] (19).

Results

A23187 Improves Hyperactivation and Fertilizing Capacity of Sperm from C57BL6 Mice.

Figure 5A:
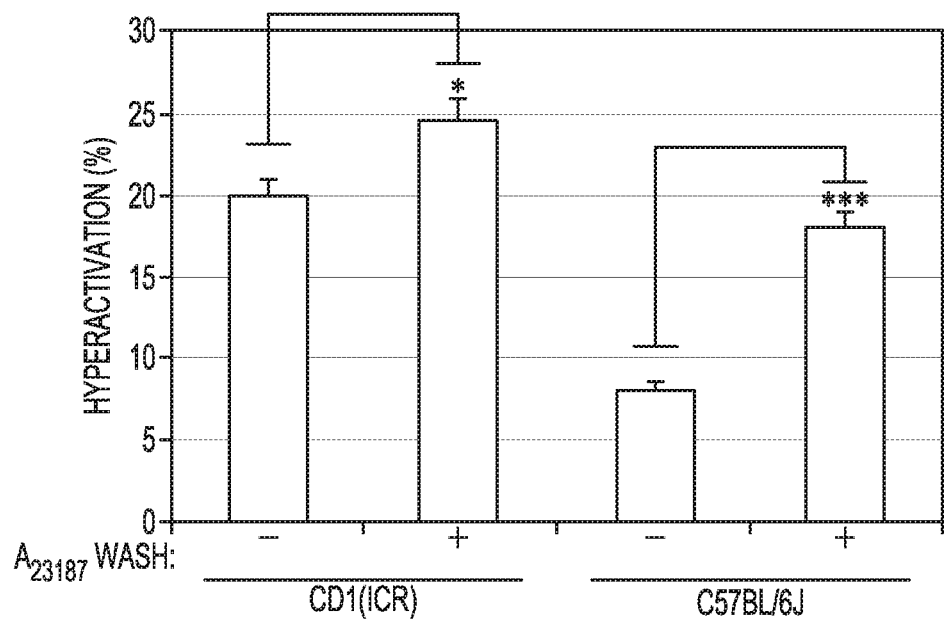
FIGS. 5A-5F show that A23187 improves hyperactivation and fertilizing capacity of sperm from B57BL6 (black 6) genetic background. Mouse sperm were incubated in Hepes-TYH (western blotting) or TYH standard (Motility and IVF assay) and KSOM for embryo culture. (A) CD-1 and C57BL6 mice sperm hyperactivation in 60 min with or without A23187 pre-treatment. (B) CD-1 and C57BL6 mice in-vitro fertilization rate with or without A23187 pre-treatment after 4 hours of insemination. (C) Developmental stage from eggs fertilized by C57BL6 sperm with A23187 pre-treatment. (D) A23187 pre-treatment over comes the fertilization inhibition by H-89. (E) PKA activation in spermatozoa with a concentration of A23187 (20 uM) pre-treatment. (F) The addition of H-89 (50 uM) inhibited PKA activation in spermatozoa with or without A23187 pre-treatment.
Figure 5B:
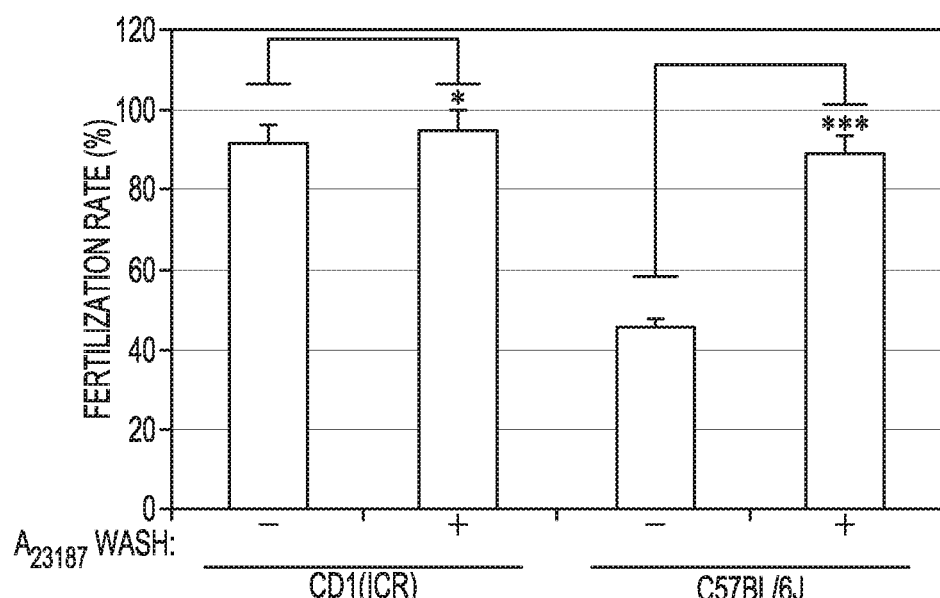
Figure 5C:
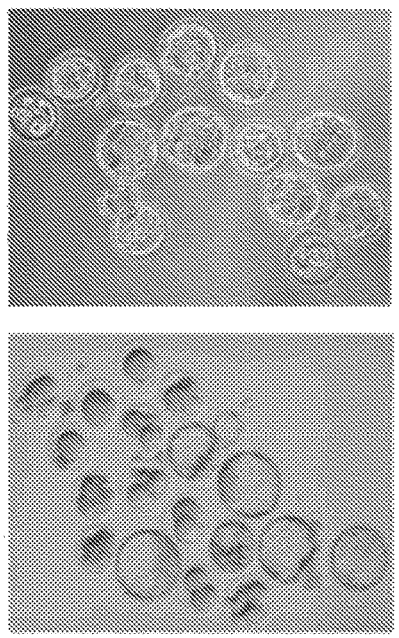
Figure 5D:
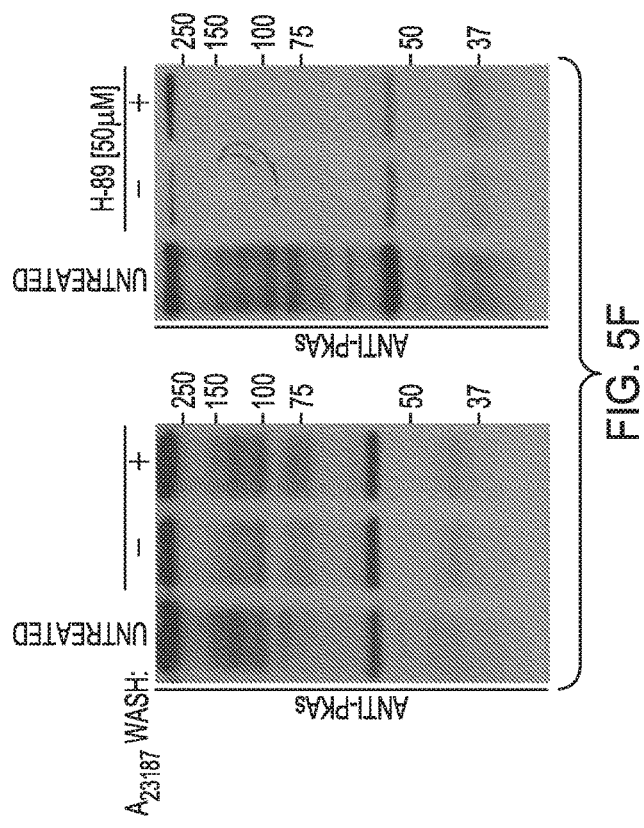
Figure 5E:
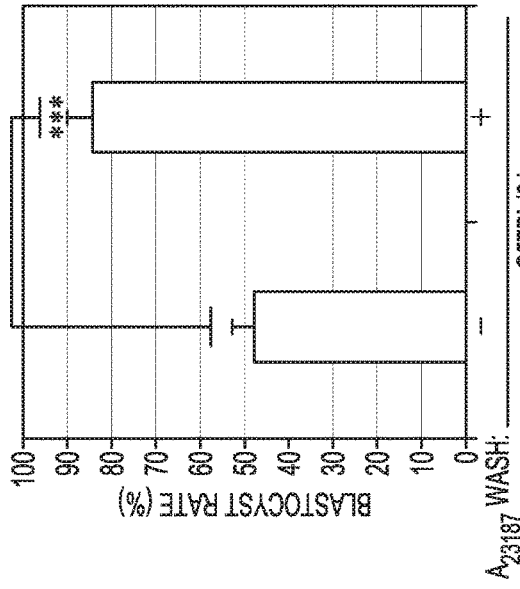
Figure 5F:
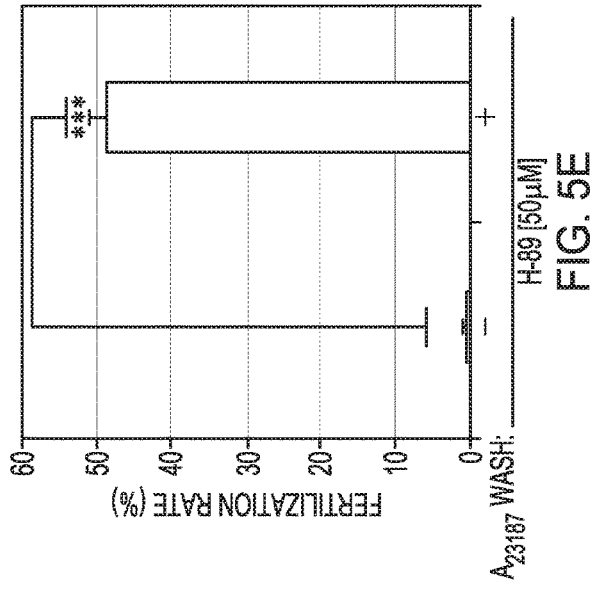

The relevance of genetic background for sperm physiology and for their ability to fertilize in vitro has been well-established (27, 28, 29, 30). Over the years, C57BL6 has been a common genetic background for studying KO genetic mouse models. Unfortunately, relative to sperm from mice of other genetic backgrounds, specifically CD1 mice, sperm from C57BL6 exhibit significantly lower hyperactivation rates when capacitated (FIG. 5 A) and are less efficient for in vitro fertilization (31) (FIG. 5B). To test the effect of a short pulse of $Ca^{2+}$ ionophore, sperm from CD1 was compared with those from C57BL6 mice. A23187 treatment increased the percentage of hyperactive C57BL6 sperm to similar levels as those obtained using CD1 sperm (FIG. 5 A). Moreover, this increase was followed by a significant increase in C57BL6 sperm fertilization rate (FIG. 5B). Two-cell derived from the use of control sperm developed to blastocysts in about 50%. This number is expected for sperm derived from this mouse strain. Surprisingly, after A23187 treatment, over 80% of fertilized eggs continued to the blastocyst stage (FIGS. 5C and D), and when non-surgically transferred to pseudo pregnant mice females, became live pups. Capacitation requires PKA activation (32), and, as expected, in the presence of the PKA inhibitor H89, C57BL6 sperm are unable to fertilize in vitro and do not show the prototypical increase in PKA substrate phosphorylation (FIGS. 5E and F). Remarkably, as seen previously with CD1 sperm, incubating H89-treated C57BL6 sperm for 10 min in A23187 was sufficient to induce fertilizing capacity (FIG. 5E), despite the fact that PKA remains inactive (FIG. 5F). These data show that transient exposure to A23187 can improve IVF success for C57BL6 mice strains and suggest this treatment has the potential to facilitate distribution of C57BL6 mouse lines.

$A_{23187}$ Treatment Induced Hyperactivation and Fertilizing Capacity of CatSper1 KO Sperm.

Figure 6A:
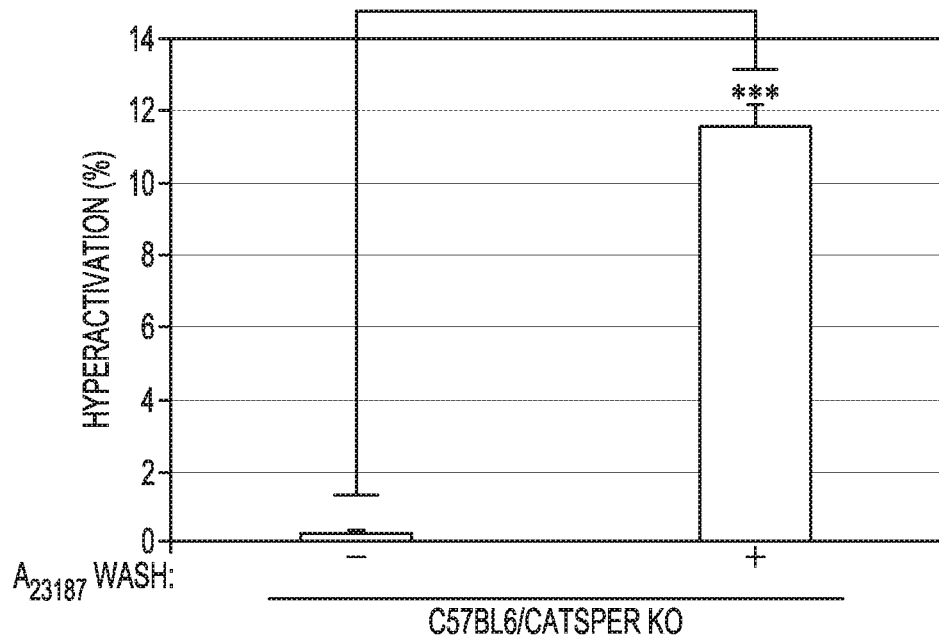
FIGS. 6A-6D demonstrate that A23187 treatment induced hyperactivation and fertilizing capacity of CatSper1 KO sperm. Mouse sperm were incubated in Hepes-TYH (western blotting) or TYH standard (Motility and IVF assay) and KSOM for embryo culture. (A) Catsper KO mouse sperm hyperactivate in 60 minutes with A23187 pre-treatment. (B) Catsper WT and KO mice in-vitro fertilization rate with or without A23187 pre-treatment. (C) Developmental stage from eggs fertilized by Catsper KO sperm rate with A23187 pre-treatment and pups obtained from Catsper KO sperm treated with A23187. (E) Genotyping of F2 Pups from Catsper heterozygous obtained from Catsper K.O rescued with A23187.
Figure 6B:
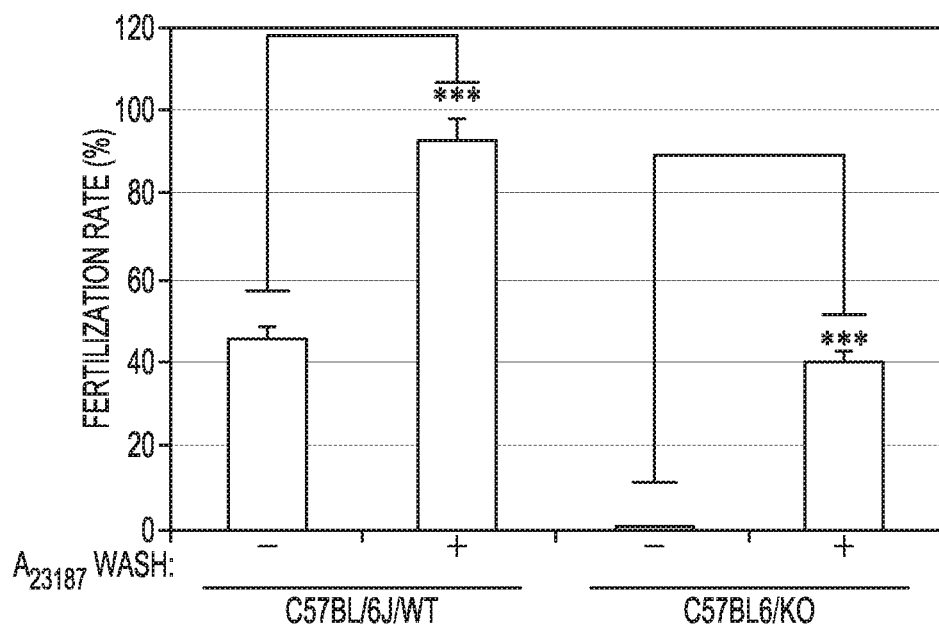
Figure 6C:
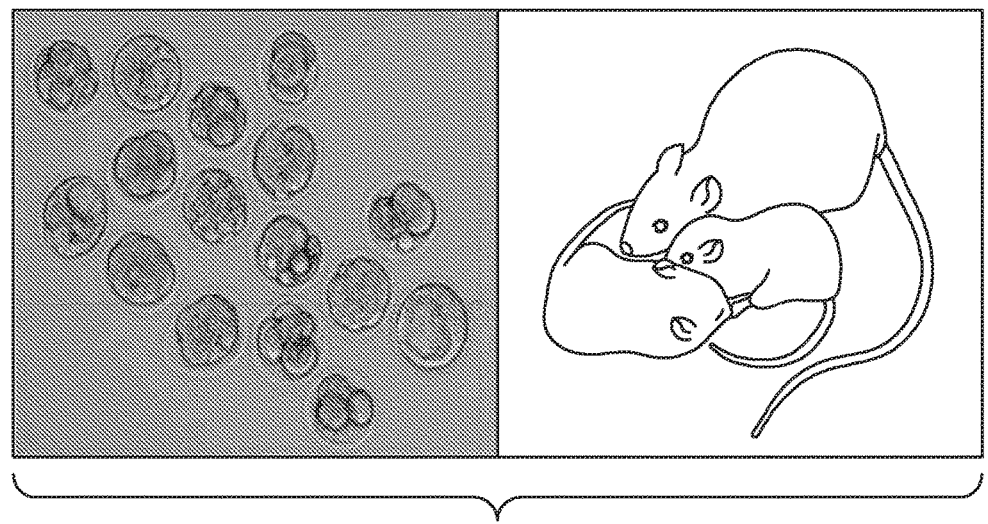
Figure 6D:
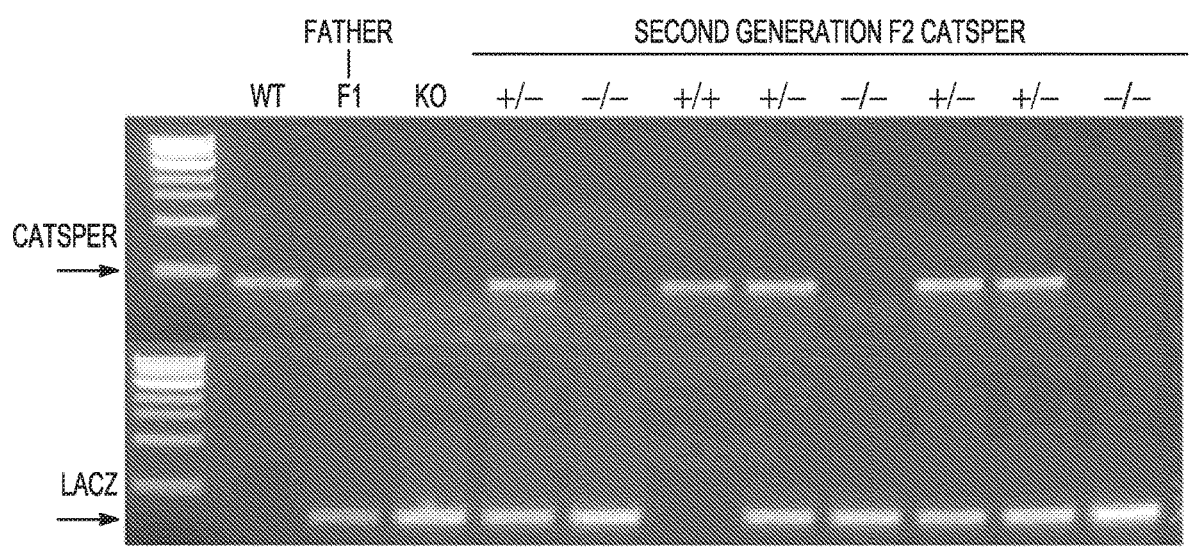

In the absence of the CatSper channel complex, sperm fail to undergo hyperactivated motility and are unable to fertilize (19). To test the extent by which $Ca^{2+}$ ionophore treatment can overcome the CatSper infertile phenotype, sperm from CatSper1 KO mice were incubated in conditions that support capacitation in the absence or in the presence of 20 μM A23187. After 10 min the sperm were washed twice by centrifugation in A23187-free media and the percentage of hyperactive sperm was measured using CASA. As expected, in the absence of A23187, CatSper KO sperm did not undergo hyperactivation (FIG. 6 A). However, once exposed to $Ca^{2+}$ ionophore, a significant number of CatSper KO sperm exhibited hyperactivated motility (FIG. 6 A). In addition, A23187-treated CatSper KO sperm were competent to fertilize metaphase II-arrested eggs in vitro (FIG. 6B). A fraction of the fertilized eggs that reached blastocyst stage were non-surgically transferred to pseudopregnant female mice (33), and five CatSper (+/−) mouse pups were born from two different females (FIG. 6C). These heterozygous F1 mice were fertile, as mating a male and female from this heterozygous population yielded a normal litter with 1 wild type, 4 heterozygous and 3 CatSper KO F2 progeny (FIG. 6D).

$A_{23187}$ Treatment Also Rescued Fertilizing Capacity in Sperm of sAC KO and SLO3 KO Mice.

Figure 7A:
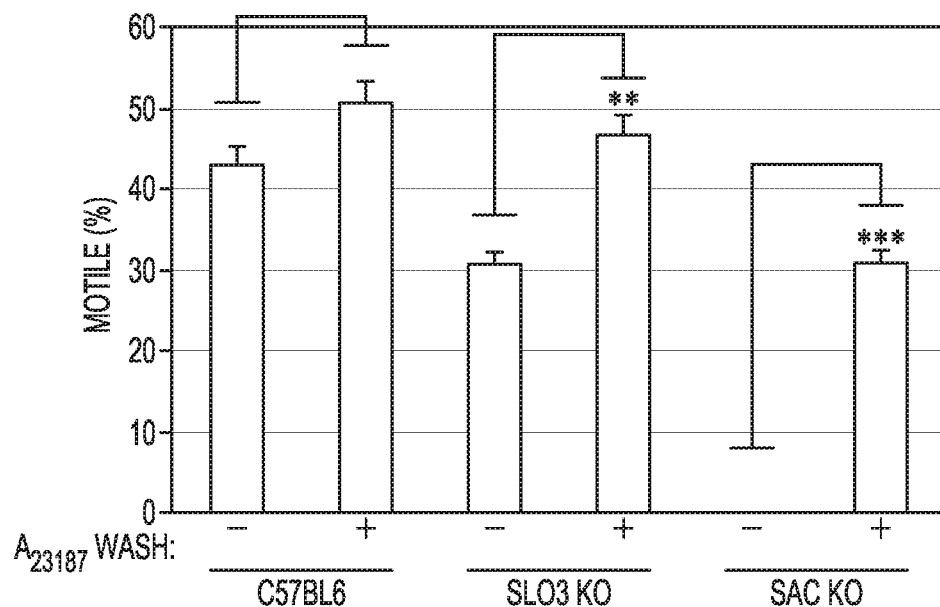
FIGS. 7A-7E show that A23187 treatment also induced fertilizing capacity in sperm from sAC and SLO3 sterile KO genetic models, but not in sperm from PMCA4 KO. Mouse sperm were incubated in Hepes-TYH (western blotting) or TYH standard (Motility and IVF assay) and KSOM for embryo culture. (A) Sperm from C57BL6, SLO3 KO, and SAC 1-2 KO were pre-treated with or without A23187 and the percentage of motility was obtained after 60 min of capacitation. (B) C57BL6, SLO3 KO, and SAC 1-2 KO sperm increase hyperactivation after 60 min upon A23187 pre-treatment. (C) Also SLO3 KO, and SAC 1-2 KO fertility rates are rescued when sperm are pre-treated with A23187. (D-E) Plasma membrane Calcium ATPase pump 4 efflux pump KO (PMC4) was used as a control. A23187 could not rescue hyperactivation and fertility rates.
Figure 7B:
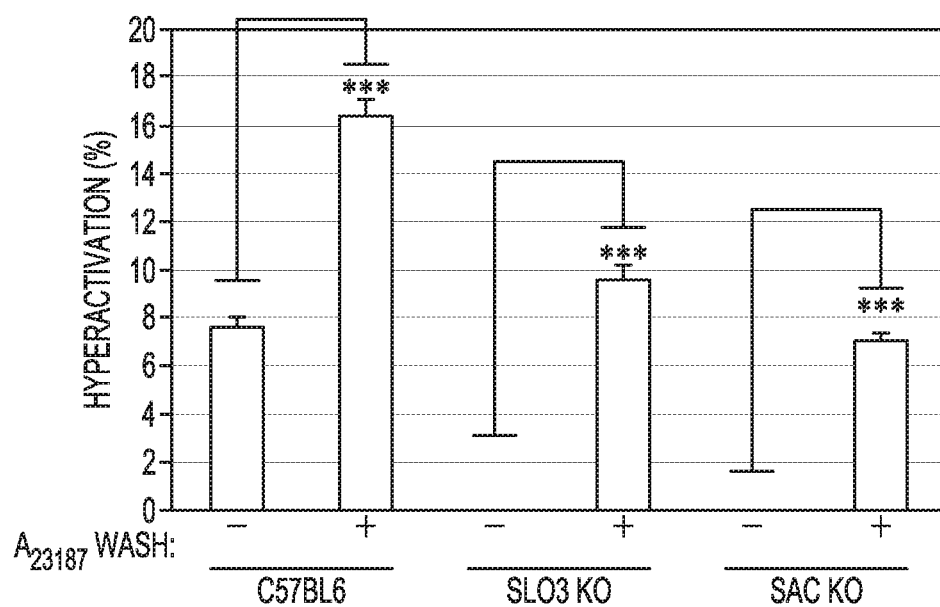
Figure 7D:
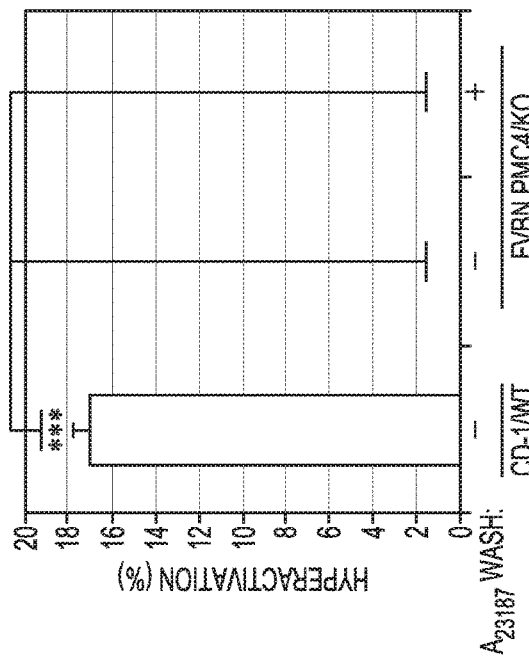
Figure 7E:
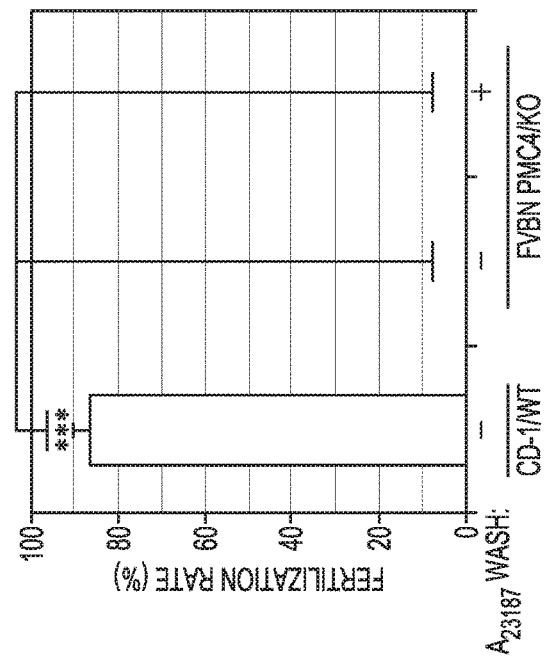
Figure 7C:
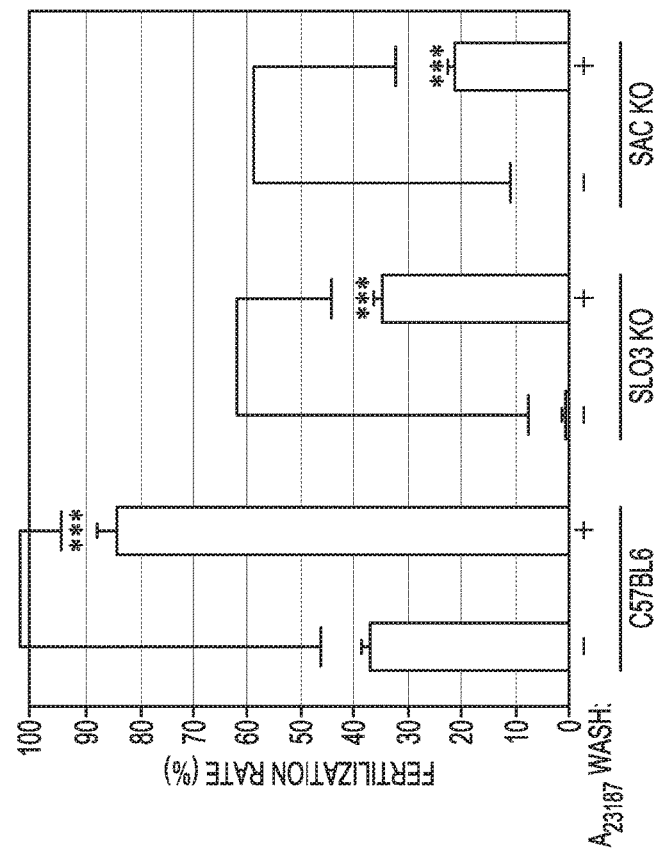

Among the earliest molecular events during capacitation are up-regulation of cAMP-dependent pathways (32) and hyperpolarization of the sperm plasma membrane (23). These events precede the essential increase in intracellular $Ca^{2+}$, and it was tested whether defects in each of these cascades can be rescued by $Ca^{2+}$ ionophore pulse. As shown above, a short pulse of $Ca^{2+}$ ionophore bypassed the need for the capacitation-induced PKA activation (1) (FIGS. 5E and F). Under normal capacitation conditions, sAC KO sperm are almost immotile (FIG. 7A), while SLO3 KO sperm are able to move. However, neither sAC KO nor SLO3 KO sperm have the ability to undergo hyperactivation (FIG. 7B). Despite this phenotype, once treated with A23187 for 10 min, a significant fraction of sAC KO sperm became motile and both sAC KO and SLO3 KO sperm underwent hyperactivation (FIG. 7B). Moreover, A23187 treatment induced fertilizing capacity in sperm from both KO models (FIG. 7C).

$A_{23187}$ Treatment does not Rescue Pmca4 KO Sperm.

It was previously shown that the increase in intracellular $Ca^{2+}$ caused by A23187 has to be followed by a reduction of intracellular calcium after removal of the ionophore (1). In sperm, two molecules are thought to mediate $Ca^{2+}$ extrusion, namely the $Na^+/Ca^{2+}$ exchanger and the more efficient sperm-specific $Ca^{2+}$ ATPase PMCA4 (34) Male PMCA4 KO mice are infertile (35), suggesting this molecule is involved in regulation of $Ca^{2+}$ homeostasis in sperm. It was hypothesized that sperm lacking PMCA4 would not respond to A23187 rescue. PMCA4 KO sperm display poor motility and do not hyperactivate (FIGS. 7 A and B). Addition of A23187 rendered all the sperm motionless and their motility was not recovered after ionophore removal (FIG. 7D). Consequently, neither their hyperactivated motility nor their fertilizing capacity was rescued (FIG. 7E).

Discussion

Capacitation encompasses a series of sequential and concomitant biochemical changes required for sperm to gain full fertilization competency. Despite the relevance of capacitation, the molecular mechanisms intrinsic to this process are not well understood. A very early event in sperm capacitation is the activation of motility by a cAMP pathway (36). The activation of cAMP synthesis occurs immediately after sperm are released from the epididymis and come into contact with high $HCO_3^-$ and $Ca^{2+}$ present in the seminal fluid (37, 38). Plasma membrane transport of these ions regulates sperm cAMP metabolism through stimulation of Adcy10 (aka sAC) (21 20, 39). sAC activation, elevates intracellular cAMP and stimulates PKA. Then, PKA phosphorylates target proteins which initiate several signaling pathways. These pathways include a sperm plasma membrane hyperpolarization, an increase in pHi, and an increase in intracellular $Ca^{2+}$ ions. Consistent with the influence of these events, KO mice genetic models in which any of these pathways is interrupted are infertile.

Physiologically, sperm capacitation is associated with changes in their motility pattern collectively known as hyperactivation and with the preparation for a physiological acrosome reaction. Originally observed in hamster sperm moving in the oviduct, hyperactivated motility (40) was later described in other mammalian species including humans (41). Hyperactivation is associated with a strong high-amplitude asymmetrical flagellar beating that appears to be essential for the sperm to loosen their attachment to the oviductal epithelium and to penetrate the zona pellucida (42). Consistent with an essential role of hyperactivation for fertilization competency, one of the most common phenotypes observed in sperm from many different infertile knock-out models including those used in the present work (e.g. CatSper, sAC, SLO3 and PMCA4) is low motility and/or defects in hyperactivation (22, 32, 38, 43, 44, 45).

Although very little is known about the molecular pathways regulating hyperactivation, $Ca^{2+}$ ions have been shown to play roles in the initiation and maintenance of this type of movement (46, 47, 48, 49). Most of the information regarding the role of $Ca^{2+}$ in hyperactivation has been obtained using loss of function approaches analyzing sperm motility in media devoid of $Ca^{2+}$ ions. Gain of function experiments using Ca$^{2+}$ ionophores (e.g. A23187, ionomycin) to increase [Ca$^{2+}$]i have yielded unexpected results because, instead of enhancing hyperactivation, these compounds stopped sperm movement (50, 51, 52). Despite being motionless, ionophore-treated sperm are alive as they recover motility after the compound is quenched with lipophilic agents (50) or washed by centrifugation (52). The reversibility of the A23187 effect suggests that the sperm is able to return to physiological [Ca$^{2+}$]i after a drop in free ionophore concentration. In previous work, it was shown that a short incubation period with A23187, in addition to initiating hyperactivation, accelerated the acquisition of fertilizing capacity. Unexpectantly, the data indicated that 10 min incubation with A23187 followed by wash out induced fertilization competence without activation of cAMP-dependent signaling pathways that are needed for capacitation (1).

Considering these results, it was hypothesized that a temporary elevation of intracellular Ca$^{2+}$ primes the sperm for hyperactivation and bypasses the need for other signaling pathways required to up-regulate Ca$^{2+}$ influx in sperm. To test this hypothesis, in the present work, four KO models affecting independent signaling pathways were selected. Three of these signaling molecules are believed to act upstream of the increase in Ca$^{2+}$ required for hyperactivation: CatSper, sAC and SLO3. Sperm from each of these mouse models are unable to undergo hyperactivation and are incapable of fertilizing metaphase II arrested eggs in vitro. In addition, PMCA4b KO sperm were used, which would not allow intracellular Ca$^{2+}$ lowering after flooding with this ion. Sperm from PMCA4b KO mice are deficient in both progressive and hyperactivated motility resulting in sterility (53, 26). PMCA4 has been shown to be the principal source of Ca$^{2+}$ clearance in sperm and it is essential to achieve a low resting [Ca$^{2+}$]i (34). Consistent with the hypotheses, a short incubation of sperm with A23187 induced hyperactivation of CatSper, sAC and SLO3 KO but not of PMCA4 KO sperm.

Male factors contribute to approximately half of all cases of infertility (54, 55). However, in over 75% of these cases it is unusual to have a clear diagnosis of the abnormalities found in semen parameters. Currently, assisted reproductive technologies (ART) remain the main therapy available. Recent studies using KO mouse models, including those used in the present work, revealed that loss of function of a variety of genes results in infertility. Interestingly, several of these models present normal sperm counts and their main deficiency is found in capacitation-associated processes such as impediments to hyperactivate (19), to undergo the acrosome reaction (56), or to go through the utero-tubal junction in vivo (57, 58). It was hypothesize that strategies designed to elevate [Ca$^{2+}$]i such as the use of A23187 pulse denoted above should overcome the need of upstream signaling pathways including but not limited to PKA activation. In addition, although IVF has been successfully employed in multiple species (6), requirements of sperm for capacitation vary greatly among species and have been developed for each sperm type essentially by trial and error. In some species, such as the horse, effective methods for IVF have still not been established despite decades of work (59). Failure of equine IVF does not appear to be associated with oocyte characteristics (60), but is associated with the inability of horse sperm to hyperactivate and to penetrate the egg zona pellucida (ZP) (61), two landmarks of capacitation. A better understanding of capacitation signaling processes have the potential to generate "universal" IVF technology that can be used in endangered/exotic species for which ART is not currently available.

Improving IVF conditions would be of great value; however, at the clinical level, ICSI has replaced IVF when confronted with cases of unknown male factor infertility. ICSI is reliable and from the patient's point of view more economical because of higher probability of success. Despite these advantages, ICSI bypasses certain aspects of normal fertilization and may bear effects that are not easily observed (e.g. epigenetic alterations). Taking this into consideration, a method to improve IVF can be a desirable option in some male factor cases. It is worth noting that A23187 has already been used in the clinic for patients with repeated ICSI failure (62). In these cases, eggs are transiently incubated with ionophore after ICSI, which exposes the zygote to high Ca$^{2+}$. On the contrary, when sperm are treated with A23187, the ionophore is washed and does not come in contact with the embryo. More interestingly, overcoming infertility problems related to motility and hyperactivation could have other potential uses in the clinic. For example, this methodology could be used to improve the success rate of intrauterine insemination which is a significantly less invasive and less costly procedure than either IVF or ICSI.

Example IV—Mouse Sperm

It is well known that out-breed and in-breed mice sperm differ in the ability to capacitate and fertilize the egg. According to the National Institute of Health (NIH-US) almost 90% of research is done in in-breed mice and the most common breed used is C57BL6. Wild type C57BL6 mice have shown low fertility in vivo compared to out-breed strains. In addition, when it comes to sperm in vitro hyperactivation and fertilization, fertility is also reduced. Therefore sperm from C57BL6 mice are a good model to show if a particular treatment can improve fertilization parameters (Navarrete et al., Sci. Rep. 2016, demonstrating that a transient exposure to calcium ionophore A23187 improves hyperactivation and fertilizing capacity of sperm from C57BL6/J mice in vitro. In the experiments presented below, C57BL6 in-breed mice strain was used.

Sperm Cell Signaling Cascades and Protein Phosphorylation:

After ejaculation, mammalian sperm are not able to fertilize, they require being in the female tract for a certain period of time which is species-specific. The physiological changes that occur to the sperm during this time period are collectively known as capacitation. Sperm capacitation can be mimicked in vitro in defined media containing: 1) ions such as Na+, Cl−, HCO3−, Ca2+ and Mg2+; 2) energy sources such as glucose, pyruvate, lactate or others; 3) a cholesterol acceptor such as bovine serum albumin (BSA) or beta-cyclodextrin. The in vitro capacitation media is used to incubate mammalian sperm before combining them with eggs during in vitro fertilization. Capacitation is associated with changes in the motility pattern. After incubation in capacitation media, sperm undergo changes in their movement known as hyperactivation. Hyperactivation motility has been associated with the sperm ability to fertilize.

Figure 8A:
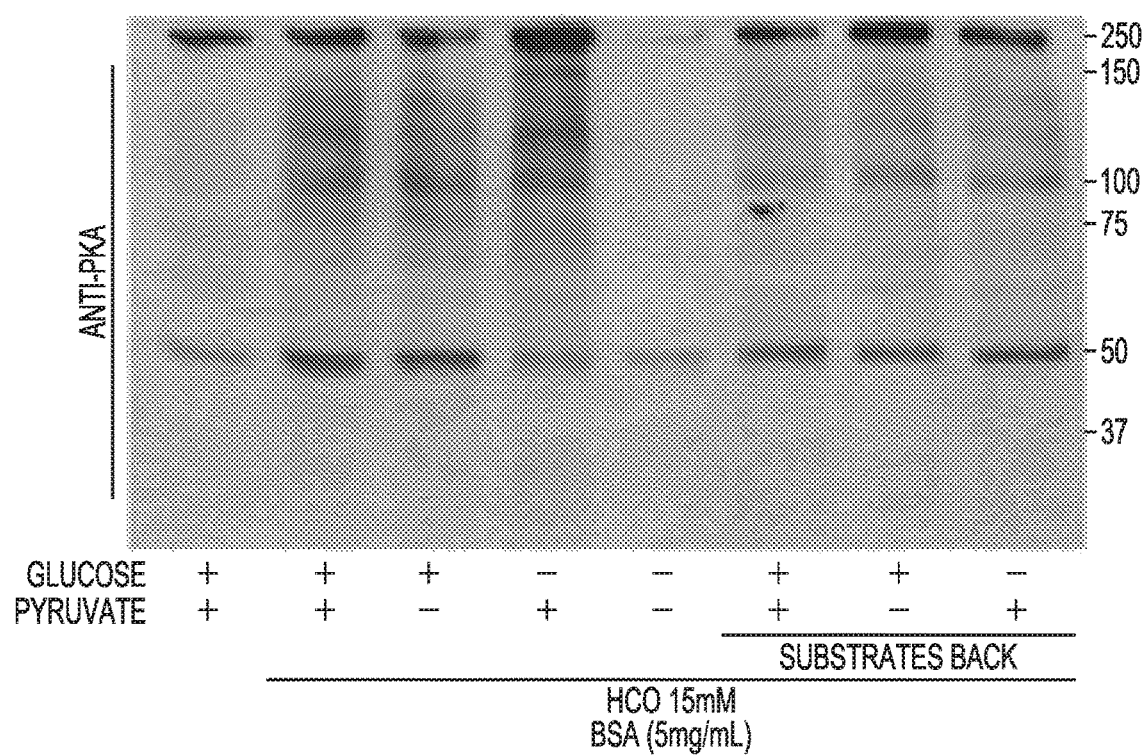
FIGS. 8A-8D depict starving conditions induced loss of phosphorylation pathways and motility. After incubation in the absence of nutrients, addition of nutrients rescued all parameters and improved motility and hyperactivation over controls. In these experiments, sperm were obtained from C57B16/j male mice. A and B. Measurement of PKA activation using anti phosphoPKA substrate antibodies (A) and the increase in tyrosine phosphorylation (B). Sperm were incubated in the absence of HCO3− and BSA (non capacitating conditions), or in the presence of these compounds (capacitating conditions) for 1 hour and in the presence or in the absence of glucose and pyruvate as indicated. After 1 hour, aliquots of sperm incubated in the absence of glucose and pyruvate (starving conditions), were supplemented with glucose (5 mM), pyruvate (0.5 mM) or both. C and D. Aliquots of sperm treated using the same protocol as described in A and B were evaluated for motility (C) and hyperactivated motility (D) using CASA.
Figure 8B:
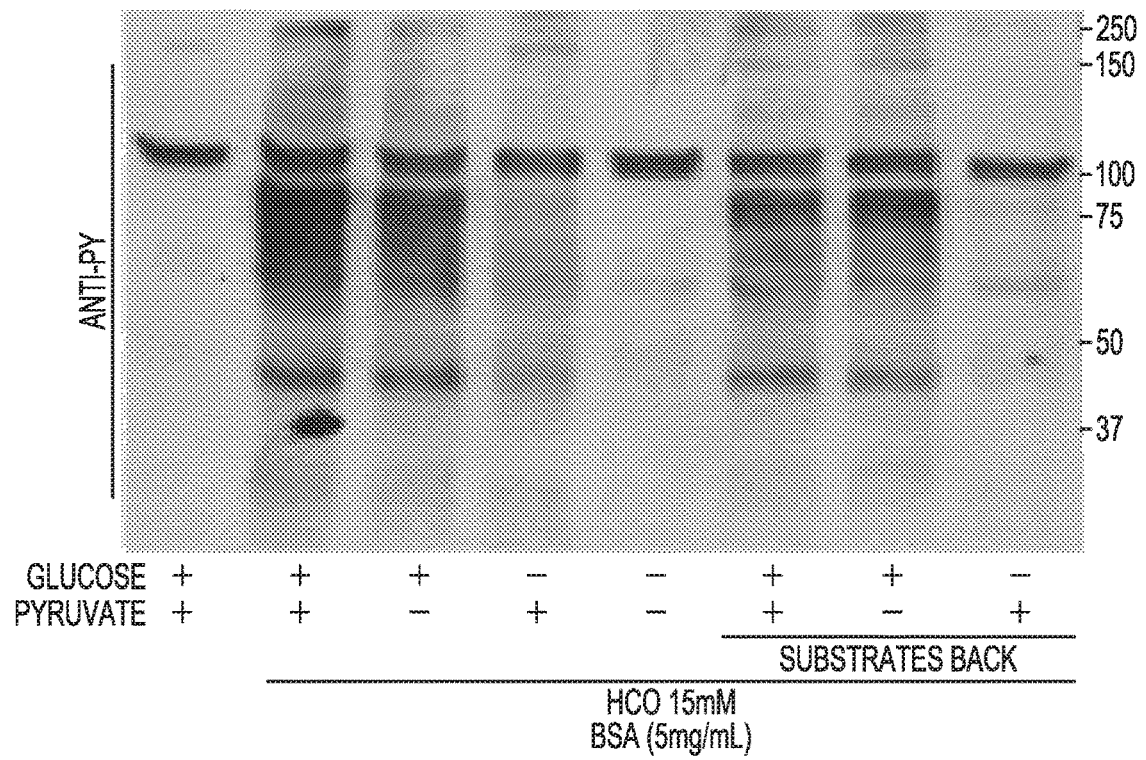
Figure 8C:
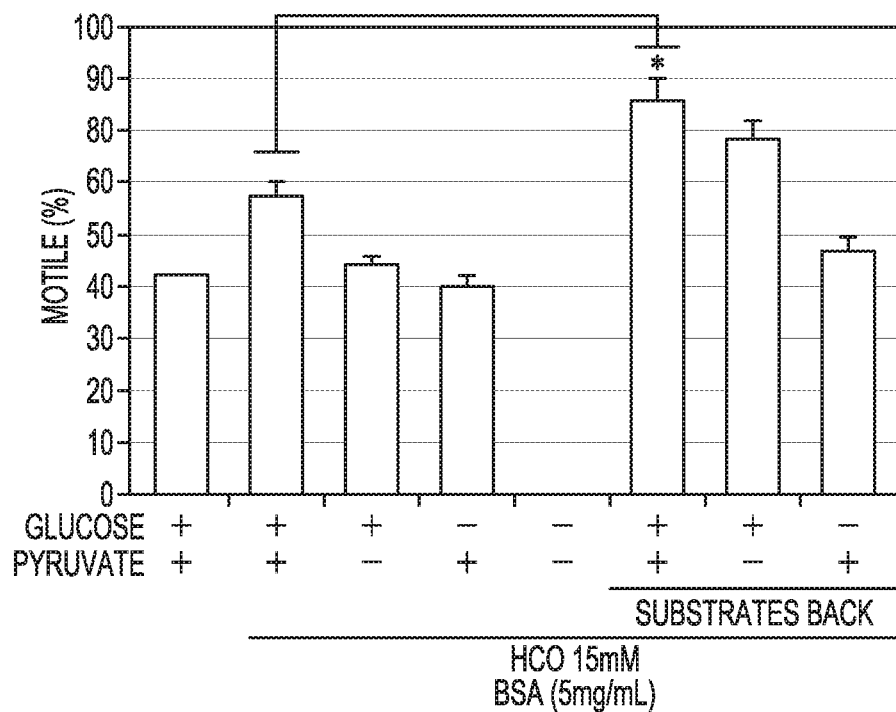
Figure 8D:
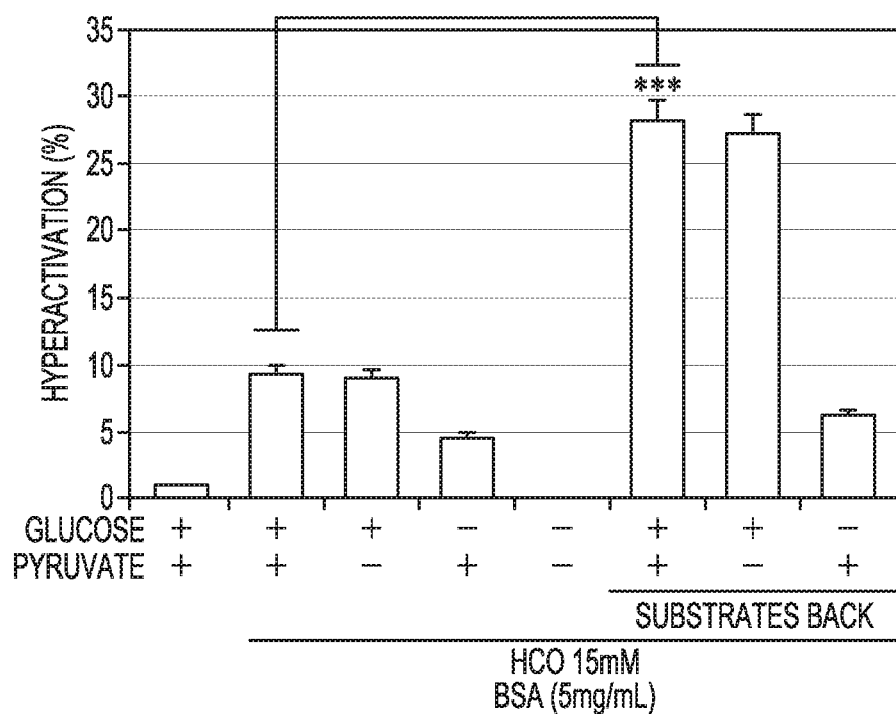

At the molecular level, capacitation is associated with a fast increase in cAMP, mediated by the atypical adenylyl cyclase Adcy10, followed by the activation of cAMP-dependent kinase, PKA. This increase in PKA is dependent on the presence of HCO3− and BSA in the capacitation media and can be measured using anti phospho antibodies against a PKA-consensus phosphorylation sequence RXXS (where X is any type of aminoacid) (FIG. 8A). Downstream of the activation of PKA, there is an increase in tyrosine phosphorylation which can be measured using anti phosphotyrosine antibodies (FIG. 8B). As shown in the figures, neither PKA activation nor the increase in tyrosine phosphorylation occur in the absence of HCO3− and BSA (lane 1 in both panels A and B). After adding HCO3− and BSA, phosphorylation patterns are activated (lane 2 in both panels A and B). In both cases, sperm are incubated in the presence of the energy nutrients glucose (5 mM) and pyruvate (0.5 mM).

The experiments depicted in FIGS. 8 A and B were performed to evaluate how the different substrates affect phosphorylation pathways. While glucose produces energy by glycolysis and might be also coupled to oxidative phosphorylation through the use of pyruvate and lactate at the end of glycolysis. Pyruvate can only be used by the mitochondria. It is shown that PKA activation occurs with both type of substrates (Lane 3 and 4 in FIG. 8A). On the other hand, the increase in tyrosine phosphorylation occurs normally with glucose as substrate (lane 3 in FIG. 8B), but it is reduced when only pyruvate is present in the incubation media (lane 4 in FIG. 8B). When sperm are incubated for 1 hour in the absence of energy nutrients, PKA activity and the increase in tyrosine phosphorylation are not observed (lane 5 in both FIGS. 8 A and B). Addition of glucose, pyruvate or both after 1 hour incubation in the absence of nutrients rescued activation of PKA (lanes 6, 7 and 8 in FIGS. 8 A and B); on the other hand only when glucose was present the increase in tyrosine phosphorylation was observed (lanes 6, 7 and 8 in FIGS. 8 A and B).

Aliquots of sperm treated as described for the phosphorylation assays in FIGS. 8 A and B, were evaluated for motility using Computer Assisted Sperm Analysis (CASA). It was observed that in the absence of nutrients for 1 hour, the percentage of motile sperm was zero. However, the motility was rescued by the addition of glucose, pyruvate or both (FIG. 8C). As mentioned above, hyperactivated sperm motility increased when sperm are incubated in capacitation conditions (presence of HCO3− and BSA), compare Bar 1 with Bar 2 in FIG. 8D. In the absence of nutrients (Bar 5 in FIGS. 8C and D), no motility is observed, and therefore, the percentage of hyperactivated sperm is also zero. When nutrients are added, hyperactivation is rescued (Bars 6, 7 and 8 in FIG. 8D). Remarkably, glucose induced significantly higher values of sperm hyperactivation after starving. This experiment suggests that upon starving, sperm can move better than when they are incubated with energy nutrients the whole time.

In vitro fertilization and embryo development is enhanced using Starving and Rescue method in young and old mice.

The significant increase in hyperactivated motility observed after rescuing sperm incubated previously in starving media (starving plus rescue) suggested that this treatment can improve fertilization rates. To evaluate this hypothesis, the fertilizing capacity of sperm incubated in control TYH capacitation media (CONTROL (C)) with sperm incubated in TYH media devoid of glucose and pyruvate and then rescued with the addition of glucose and pyruvate (STARVING+RESCUE (S+R)) were compared. In mice, like in humans, decreased fertility has been observed in aged individuals, and it is caused by different factors such as diet, exercise and genetic outcomes. A recent study has shown the effects of advanced paternal age on mice reproduction. Interestingly, the authors concluded that fertilization capacity (natural conception) is reduced when mice reach 12 months of age and it declines after that age. Remarkably, they also discover that IVF, in vitro embryo development, and embryo quality were also affected with age. Taking this into consideration, our experiments were conducted using male mice of three different age groups: 3-6 month old, 6 to 12 month old, and 12-24 months old. For oocyte donors, young females were used (2 months old).

Figure 9A:
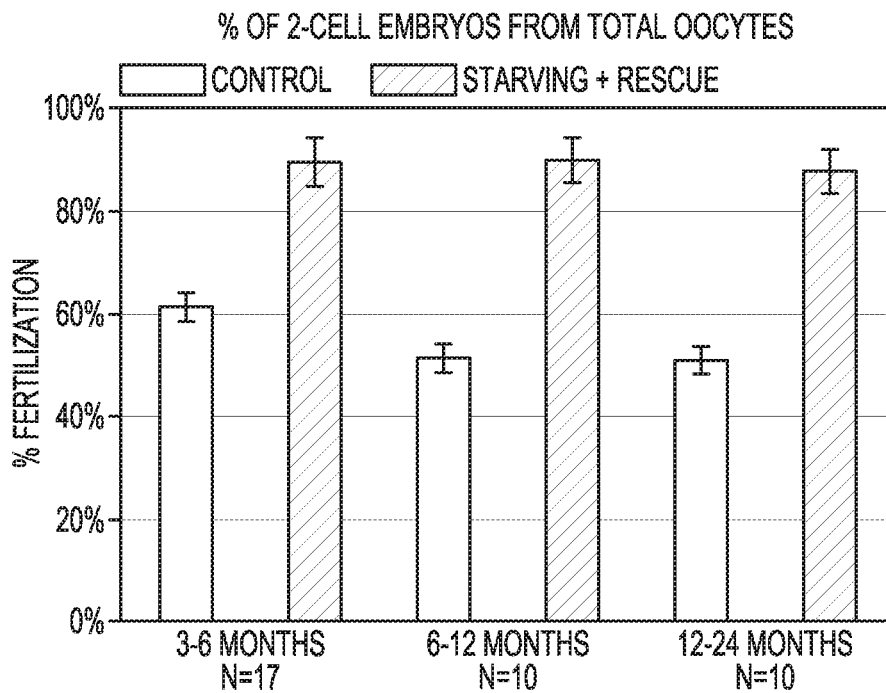
FIGS. 9A-9F depict starving plus rescue sperm incubation increased fertilization rates and embryo development rates in mouse sperm. Sperm obtained from C57BL6 mouse strain from different age mice (as shown in figure) were incubated in capacitating TYH media in the presence (control) or in the absence of glucose and pyruvate (starving+rescue). After 40 min, sperm in starving conditions are rescued by addition of glucose (5 mM) and pyruvate (0.5 mM). Sperm in both conditions are left for additional 20 min and then added to the insemination droplet containing cumulus enclosed CD1 oocytes (A, B and C) or C57BL6 (D, E and F). Number of repetitions (independent mice) is given below each treatment. Percentage of fertilization considers the number of oocytes that achieved 2-cell stage (A and D). 2-cell embryos are then transferred to KSOM media and further incubated for additional days. Percentage of blastocyst is calculated either by considering the number of 2-cell embryos (B and E) or by considering the initial number of oocytes (C and F).
Figure 9B:
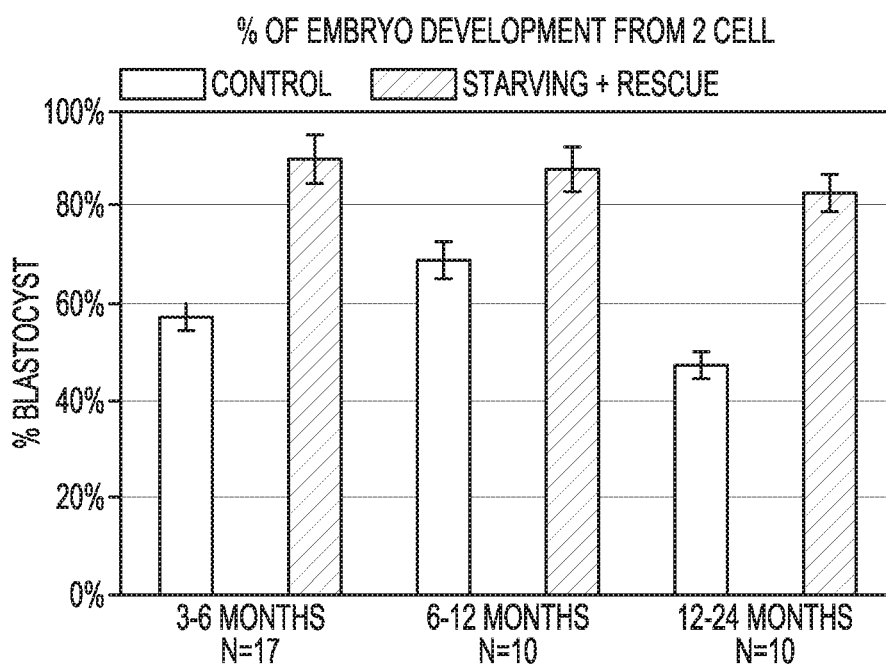
Figure 9C:
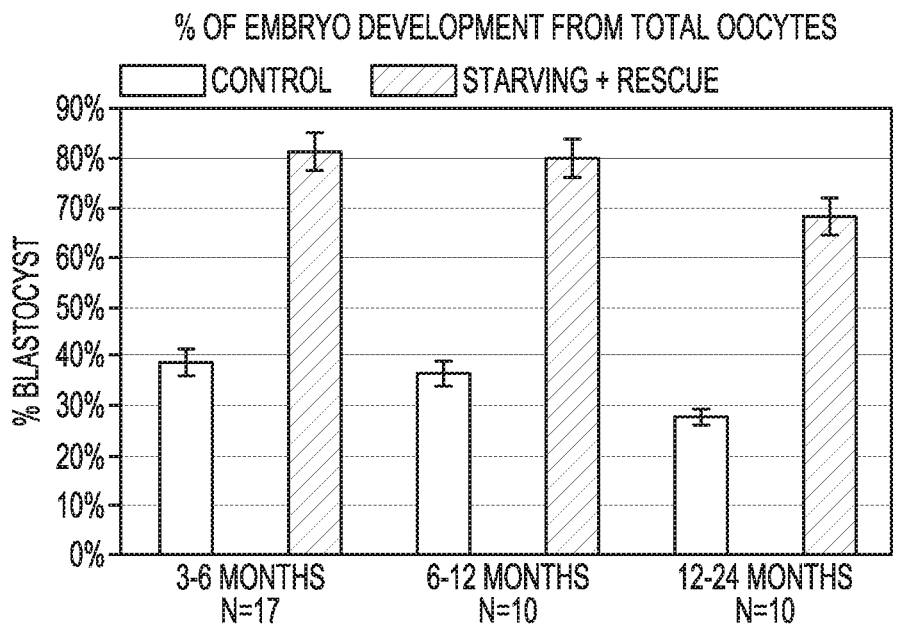
Figure 9D:
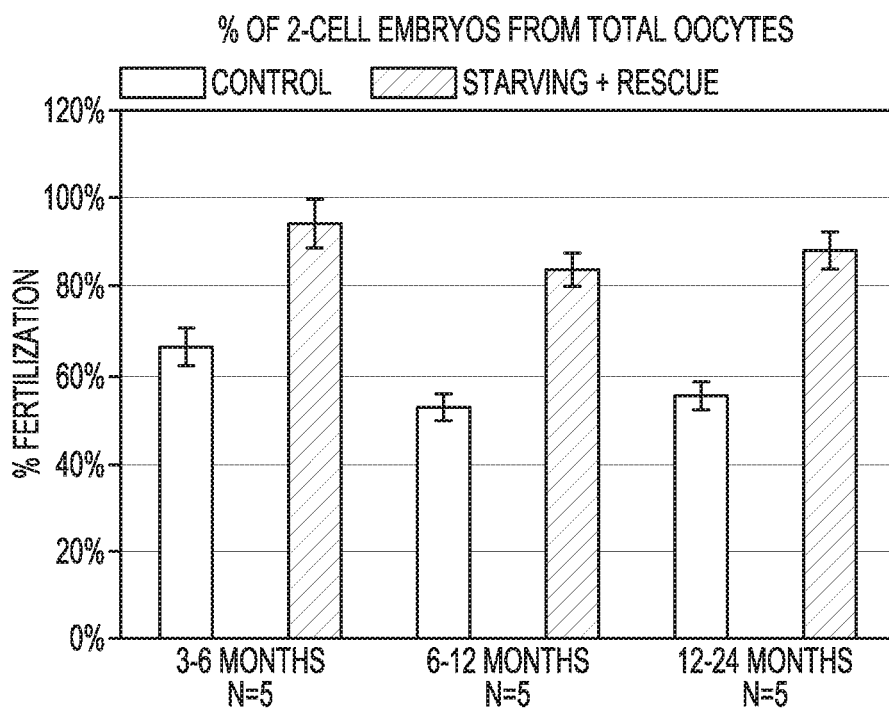
Figure 9E:
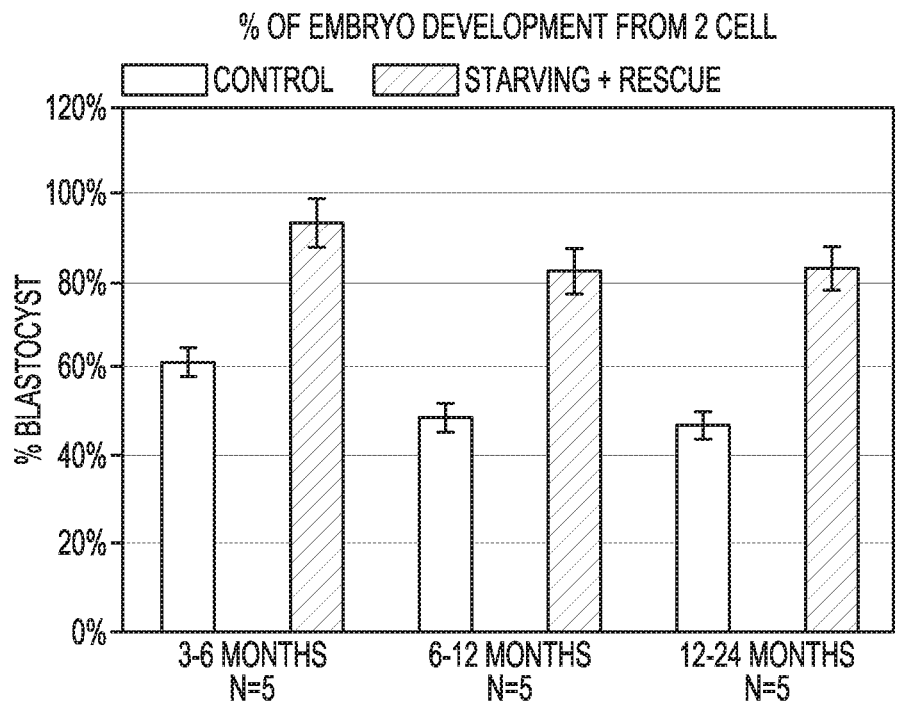
Figure 9F:
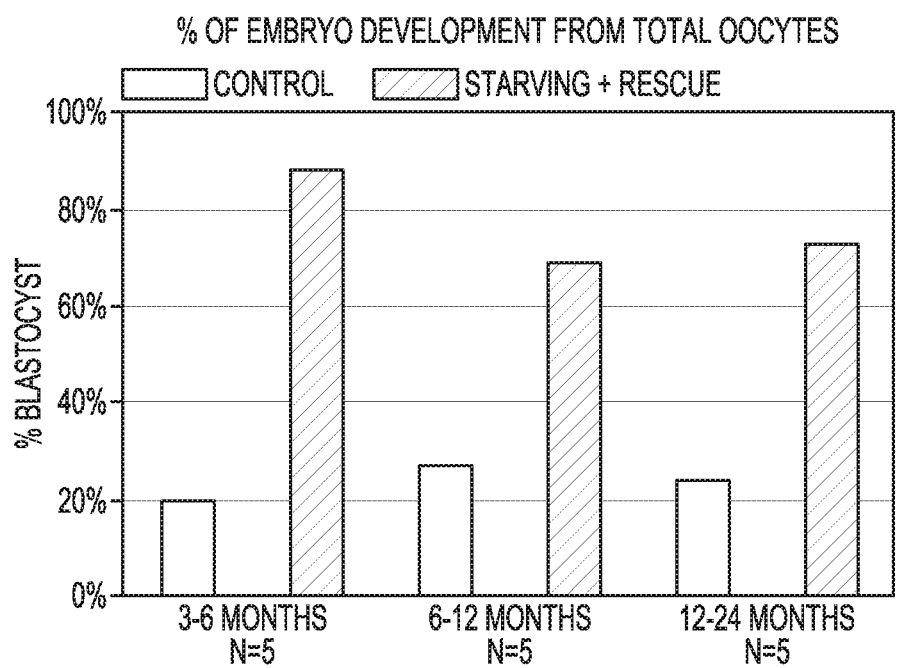

Initially these experiments were done using CD-1 oocytes (FIGS. 9 A, B and C) and then repeated with oocytes obtained from C57BL6 mouse strain (FIGS. 9D, E and F). The rationale of trying both types of oocytes is that C57BL6 oocytes are not as good in fertilization protocols as the CD-1 oocytes. It was observed that the percentage of fertilized oocytes (measured by the percentage of oocytes arriving to 2-cell embryos) was increased when sperm are treated in S+R conditions (FIG. 9 A). The higher fertilization rates were maintained regardless the age of the mice (3-6; 6-12, and 12-24 months old). Two-cell embryos obtained in each condition were then transferred to KSOM media for further embryo development. Surprisingly, the percentage of blastocysts achieved from two-cell embryos obtained using S+R sperm was higher than the ones fertilized with C sperm (FIG. 9B). Notice that in FIG. 9B, the percentage of blastocyst development is calculated from the total amount of two-cell embryos in each condition. If the percentage of blastocyst development was plotted considering the initial number of oocytes, it is possible to observe that the S+R treatment is highly efficient when compared with standard media (FIG. 9C). Improvement in the percentage of fertilization and embryo development was also observed when C57BL6 oocytes were used (FIGS. 9D, E and F).

Experiments were then conducted to evaluate the speed by which sperm treated in standard conditions or starved and then rescue can fertilize CD1 oocytes. Table 1A, first column, shows the incubation time of sperm with eggs for each treatment (control or starving+rescue) (second column). After this time period, eggs were removed, washed and continue the incubation in fertilization media. The number of two-cell embryos was evaluated the following day. The data presented in each of the columns indicate the number of oocytes (Oocytes #), the number of oocytes reaching two-cell embryo stage (cleavage) with the respective percentage between parenthesis, the number of two-cell embryos reaching blastocyst stage (Blastocyst) with the respective percentage compare with the initial number of two-cell embryos, and, finally, the percentage of blastocysts taken into consideration the initial number of oocytes in the assay (Total % blastocyst). In this table, it is possible to observe that the starving plus rescue conditions increased the velocity of fertilization.

Table 1 A and B. Comparison of standard and Starving plus Rescue sperm treatment regarding the speed of fertilization and the minimum amount of sperm needed for insemination in vitro.

TABLE 1A

| Time (Min) | Treatment | Oocytes # | Cleavage (%) | Blastocyst (%) | Total % Blastocyst |
|---|---|---|---|---|---|
| 15 | Control | 298 | 23 (8) | 15 (65) | 5 |
| 30 |  | 278 | 91 (33) | 64 (70) | 23 |
| 60 |  | 315 | 176 (56) | 89 (51) | 28 |
| 240 |  | 134 | 106 (65) | 61 (61) | 36 |
| 15 | Rescue | 285 | 111 (39) | 92 (83) | 32 |
| 30 |  | 307 | 181 (59) | 159 (88) | 52 |
| 60 |  | 298 | 250 (84) | 225 (90) | 76 |
| 240 |  | 112 | 98 (87) | 87 (88) | 78 |

TABLE 1B

| # Sperm Cells | Treatment | Oocytes # | Cleavage (%) | Blastocyst (%) | Total % Blastocyst |
|---|---|---|---|---|---|
| 500 | Control | 235 | 54 (23) | 29 (54) | 12 |
| 1000 | | 260 | 80 (31) | 45 (56) | 17 |
| 10000 | | 245 | 88 (36) | 33 (38) | 13 |
| 100000 | | 98 | 58 (60) | 39 (67) | 40 |
| 500 | Rescue | 281 | 142 (47) | 96 (73) | 34 |
| 1000 | | 220 | 145 (66) | 107 (74) | 49 |
| 10000 | | 255 | 181 (71) | 152 (84) | 60 |
| 100000 | | 103 | 92 (90) | 82 (89) | 80 |

A similar experiment was conducted to evaluate the minimum number of sperm needed for fertilization. This experiment is presented in Table 1B. For this experiment, sperm incubated in control (Control) or in starving plus rescue (Rescue) media were counted and then a series of dilution of the original sperm suspension were done with the purpose of adding different number of sperm to the insemination drop as detailed in column 1. The columns present the same information described for Table 1A: number of oocytes, number of two-cell (percentage), number of blastocysts (percentage with respect to the number of two cells), and total % blastocyst with respect to the initial number of eggs. Data in Table 1B indicates that fertilization can be achieved with lower sperm number.

Figure 10A:
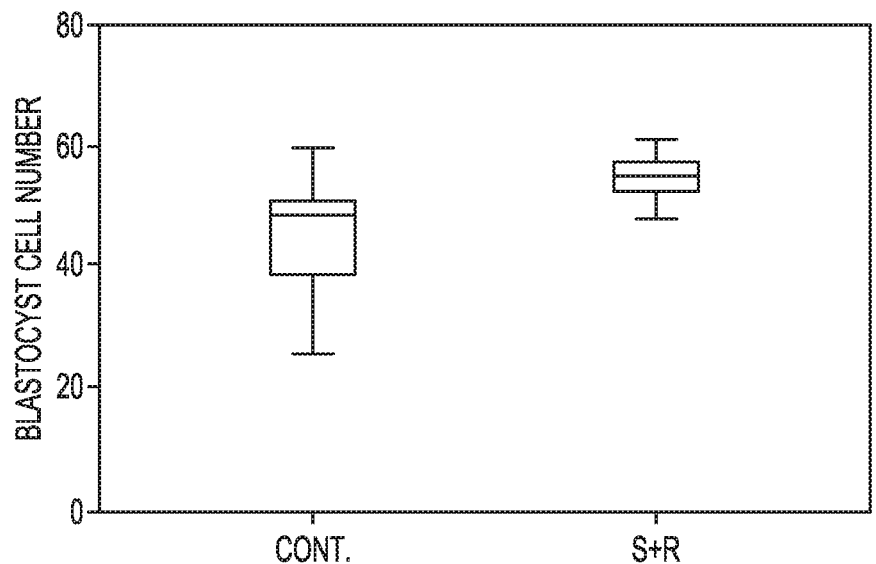
FIGS. 10A-10D depict starving plus rescue method improves blastocyst cell number, outgrowth and number of pups per embryo transferred. A. Blastocyst cell number. Sperm were incubated in control or starved plus rescue (S+R) conditions and used for in vitro fertilization. Two-cell embryos were then transferred to KSOM media and further incubated for a total of 3.5 days. Blastocysts were then stained with Hoecsht and the number of cells in each blastocyst counted. Numbers represent the average±SEM (n=10). B. Blastocyst in vitro outgrowth. Blastocysts obtained with control or starved plus rescue sperm were assayed for outgrowth in vitro (n=10). C. Litter size obtained with the different treatments analyzed by age group. Blastocysts obtained from sperm incubated in control or starved plus recue conditions were transferred to pseudo-pregnant females. The analysis was done separating the results into two groups (sperm form mice 2-12 month old (n=15) and sperm from mice 12-24 month old (n=8). Each data point is presented in the graph. D. Percentage of pups per number of embryos transferred. The same data were analyzed considering the number of pups that were born considering the respective number of blastocysts transferred in each case. Each data point is presented in the graph.
Figure 10B:
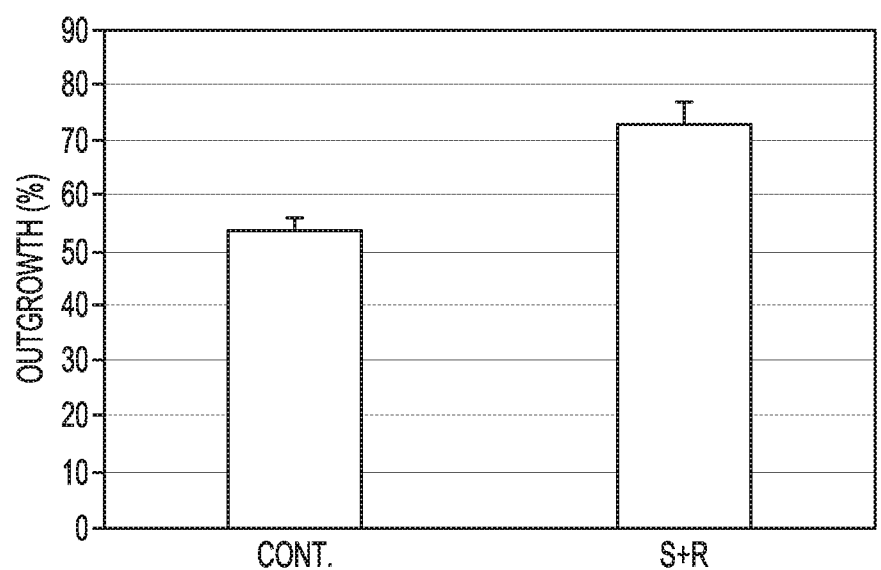
Figure 10C:
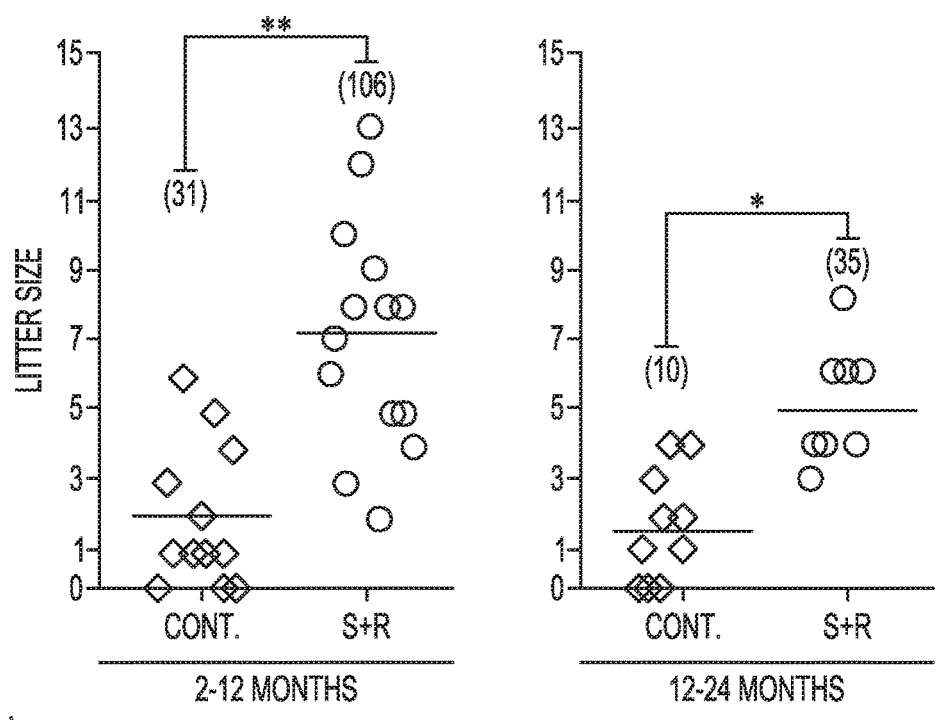
Figure 10D:
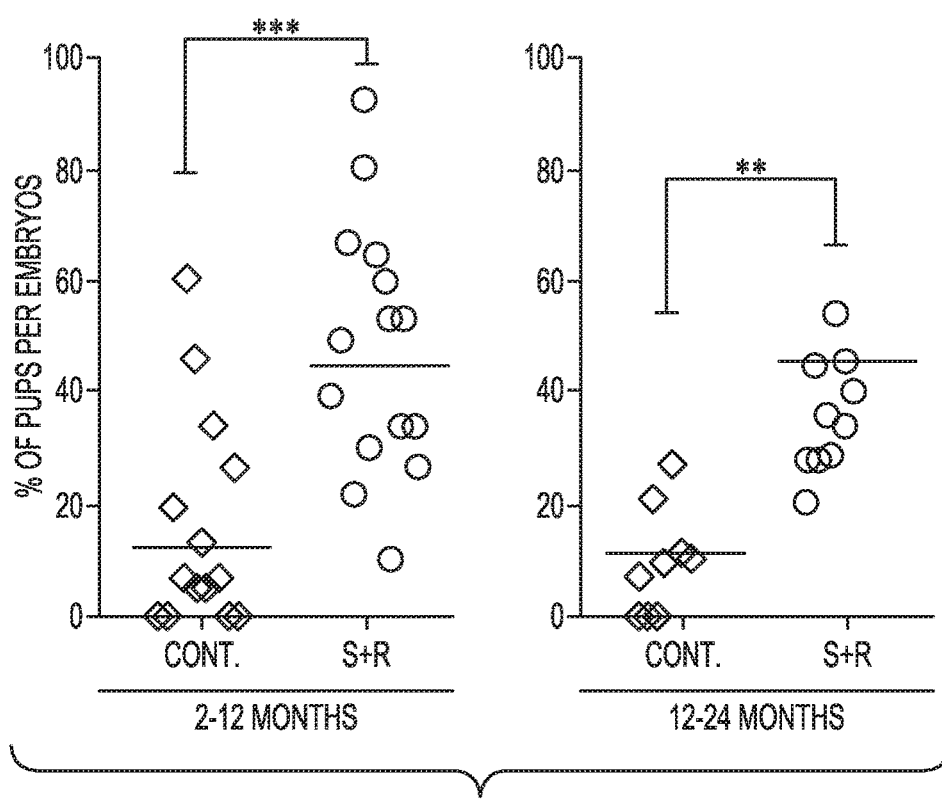

Since the first successful IVF in mammals, it has become clear that there is a direct relationship between embryo quality and gestational success post embryo transfer. Different studies have shown that IVF have an impact on embryo development in vitro. Considering that the starving methodology improved fertilization rates and also increased the number of blastocysts, it was decided to compare quality of blastocysts obtained with the different methodologies by counting the number of cells present in 3.5 blastocysts. For each condition, 35 blastocysts obtained from 10 individual experiments were evaluated. The total number of cells was assessed by counterstaining of nuclei and served as an indicator for division rates. While control sperm produced blastocysts with an average of 46 cells, starved and rescued sperm produced blastocysts with an average of 55 cells (FIG. 10 A). Blastocysts were further assessed by three-day outgrowth (OG) assay to test hatching, attachment and formation of the inner cell mass (ICM) with surrounding trophoblast cells in an in vitro system. An n=10 outgrowth assays were done from different 10 IVF experiments, and a total of 200 blastocyst were recorded for each of the sperm treatments. Control blastocyst outgrowth showed a significantly lower embryo attachment to the petri dish (55%) than the Starving plus rescue treatment (75%) (FIG. 10B). The next step to evaluate embryo quality from 3.5 blastocyst embryos obtained with different sperm was to perform embryo transfer to pseudo-pregnant mice females. 25 independent experiments were evaluated. For each experiment, the same number of 3.5 day blastocysts obtained with sperm treated either with control media or with starving plus rescue protocol were transferred non-surgically. Because, more blastocysts were obtained routinely using the starving plus rescue protocol, for these experiments, the number of blastocysts transferred was always limited by the amount of blastocysts obtained with control-treated sperm which range between 8 and 16 blastocysts. After transfer, the females become pregnant and the litter size for each condition was recorded (FIG. 10C). Results were analyzed depending on the mice age (2-3 months old vs 12-24 months old). As shown in FIG. 10C, the average litter size for embryos obtained using Starving plus Rescue sperm treatment was significantly higher for both age groups. The data were also analyzed as percentage of pups per number of blastocysts transferred (FIG. 10D). Altogether these data indicate that blastocysts obtained using starved plus rescued sperm have better quality than those obtained using standard control conditions.

Figure 11A:
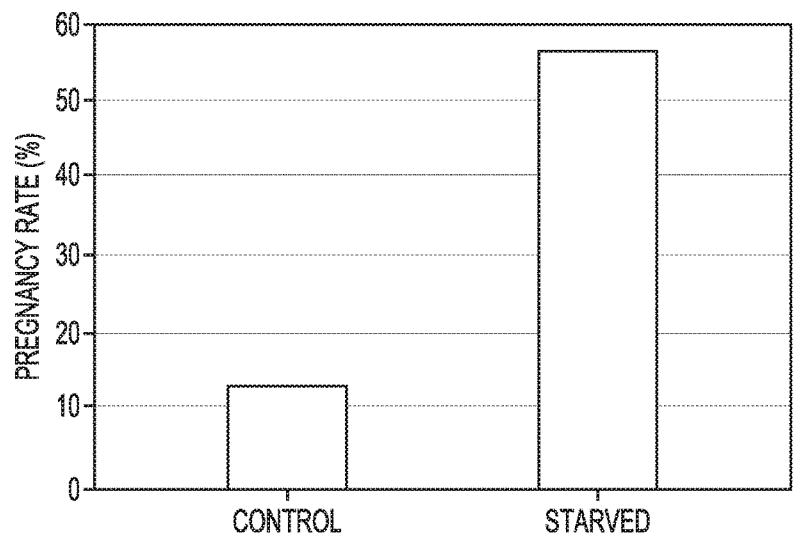
FIGS. 11A-11C. IUI is improved using starved sperm. Sperm from C57BL6 mice were incubated in control media or in starving media (starved). Once sperm are not moving (about 40 min), sperm are transferred non-surgically to pseudo-pregnant females. A. percentage of females that become pregnant after IUI with sperm incubated in either control or starved media. B. Average litter size±SEM (n=10). C. Example of pups obtained by IUI using starved method.
Figure 11B:
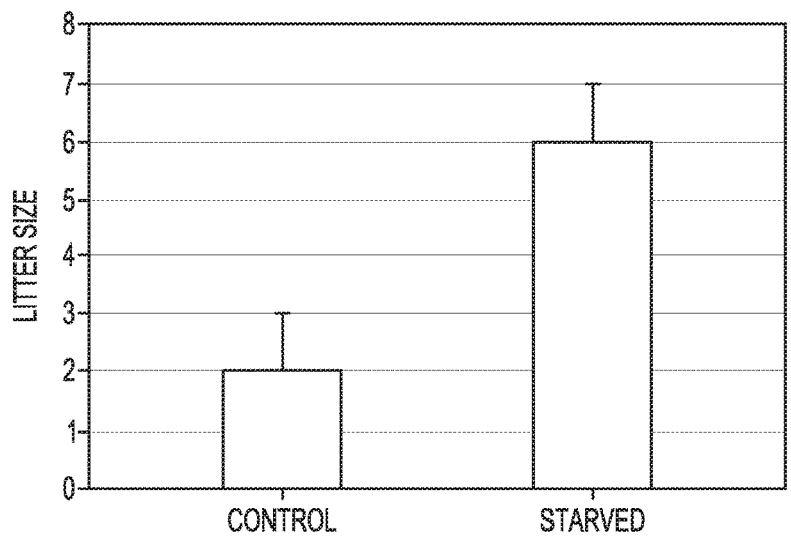
Figure 11C:
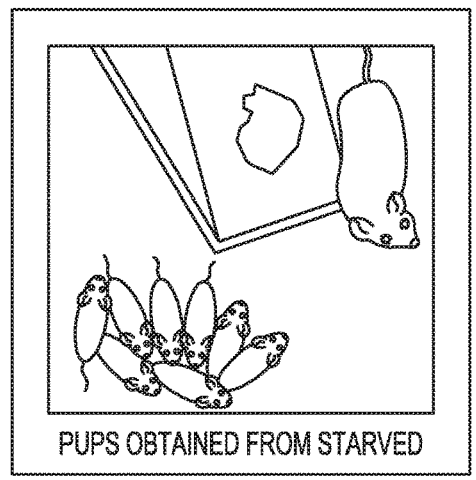

Intrauterine insemination (IUI) is an assisted reproductive technique that delivers sperm into the female tract bypassing the cervix. IUI is implemented in humans as a fertility treatment, and widely performed in commercial breeding of livestock. However, in the literature there is few studies about IUI in mouse compared with other species such as humans, bovine, horses and many others. Therefore, it was decided to evaluate the success of sperm using control media vs the success of sperm treated with the starving protocol. In IUI protocol, the rescue of sperm was not done; the sperm were used directly after incubation in media without nutrients (starving). Because IUI in mice has been shown to work better when sperm are incubated in non-capacitating conditions, the media used for these experiments for both control and starving conditions was done without addition of $HCO_3^-$ and BSA. Success of IUI in mice depends on two main variables. The first one is the number of females that becomes pregnant with respect to the total of females inseminated (FIG. 11 A). The second one is the litter size in those females that become pregnant (FIG. 11B). As an example pups obtained in one of the IUI experiments using starved plus rescue protocol are shown (FIG. 11C).

As mentioned above, in-breed genetic backgrounds have lower fertility in vivo and in vitro. These mice strains such as C57BL6 are relevant for research and high priority on the mouse phenome database. In addition genetic manipulation of these valuable mice leads in many cases to acute sub-fertility. It was decided to use two knock out (KO) models (FerTDR/DR and Akita) and one in-breed mouse (SJL/J) with proven sub-fertility in vitro. As it was shown previously calcium ionophore A23187 overcome mice infertility in different KO models; therefore, for FerT KO, A23187 treatment was also used to compare the success rate of different treatments. FerT sperm fertilization rate was improved with A23187 transient incubation. However, starving treatment improves fertilization of FerTDR/DR sperm to higher levels (FIG. 12 A). In both treatments, two-cell embryos were transferred to KSOM media and further incubated for 3.5 days. Results indicate that once two-cell are obtained, both ionophore treatment and starving plus rescue protocols are equally successful for embryo development (FIG. 12B). Similarly, starving plus rescue improved fertilization rates of sperm from Akita and SJL/J mice (FIG. 12C). In one of the experiments using FerTDR/DR and one using Akita mice, blastocysts obtained using starved plus rescue protocol were transferred and pups were obtained (10 for FerTDR/DR and 5 for Akita) (data not shown).

Figure 13A:
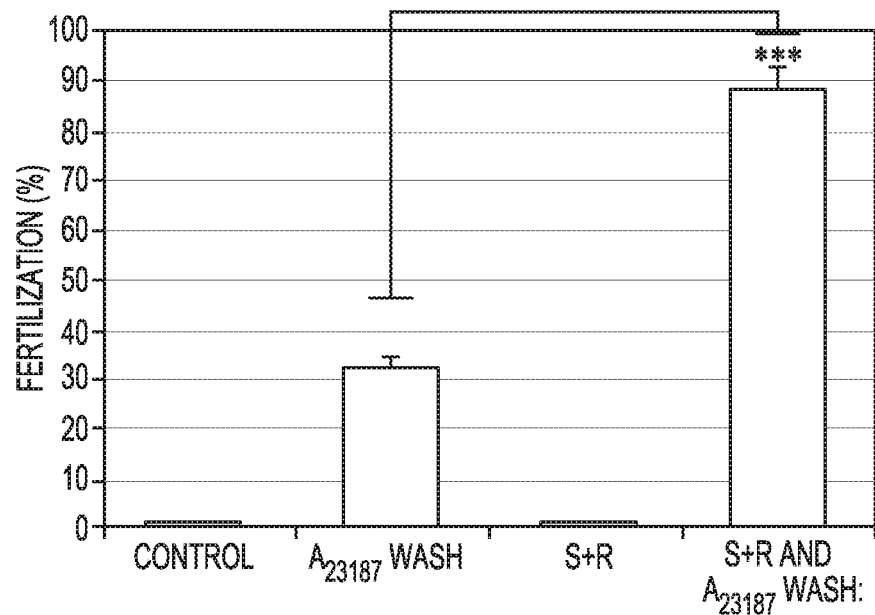
FIGS. 13A-13B. Combination of starved plus rescued protocols with the transient exposure to CA2+ ionophore A23187 rescued the completely sterile phenotype of CatSper KO mice. A. Fertilization Rate. Sperm from CatSper1 KO mice were incubated in four different conditions: 1) control; 2) A23187 transient treatment; 3) starved plus recue treatment; and 4) starved plus rescue treatment followed by A23187 transient treatment. B. Blastocyst development. Two-cell embryos obtained in A were transferred to KSOM media and further incubated for 3.5 days. The percentage of blastocyst with respect to the two-cell embryos are presented. In both A and B, the results presents the average±SEM form 4 independent CatSper KO mice (n=4).
Figure 13B:
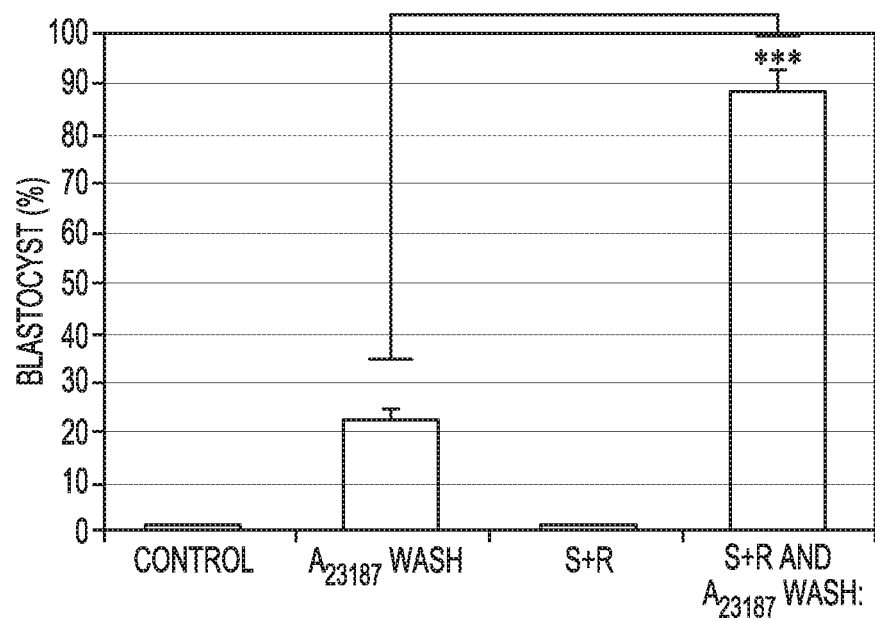

Many genes have been shown to play a role in fertilization. A group of genes code for the sperm-specific calcium channel complex CatSper. Knock-out mice lacking any of the four main CatSper subunits (CatSper1, CatSper2, CatSper3 or CatSper4) are infertile in vivo and in vitro. A short treatment with calcium ionophore A23187 induces fertilization capacity in sperm from these mice. Using this technique combined with embryo development and embryo transfer pups were obtained (Navarrete et al., Sci. Rep. 2016). To investigate if the starving plus rescue technology was also able to rescue the infertility phenotype, sperm were incubated in four different conditions: 1) Control; 2) A23187 transient treatment; 3) starved plus rescue treatment; and 4)

starved plus rescue treatment followed by A23187 transient treatment. After these treatments, sperm were combined with eggs and the number of two-cell embryos developed counted (FIG. 13 A). The use of A23187 rescued the infertile phenotype. On the other hand, starved plus rescued sperm incubation protocol did not rescue infertility. However, when both treatments were combined the CatSper fertilization rate was close to 90%. In each of these experiments, two-cell embryos were transferred to KSOM media and further incubated for 3.5 days. Blastocyst were then counted and plotted as percentage of blastocyst in relation to the number of two-cell embryos (FIG. 6B). In this case, the A23187 transient treatment achieved 20% development and the combined starved plus rescue with A23187 transient treatment was close to 90%. From these experiments, a total of 15 blastocysts from each treatment were transferred into 2.5 days pseudo-pregnant females. A23187 alone gave birth to three heterozygous pups and the starved plus rescue protocol gave birth to six heterozygous pups. Altogether, these results suggest that combination of treatments is very effective in producing healthy embryos and that it can be used as treatment in some infertility cases.

Example V—Bovine Sperm

Figure 14A:
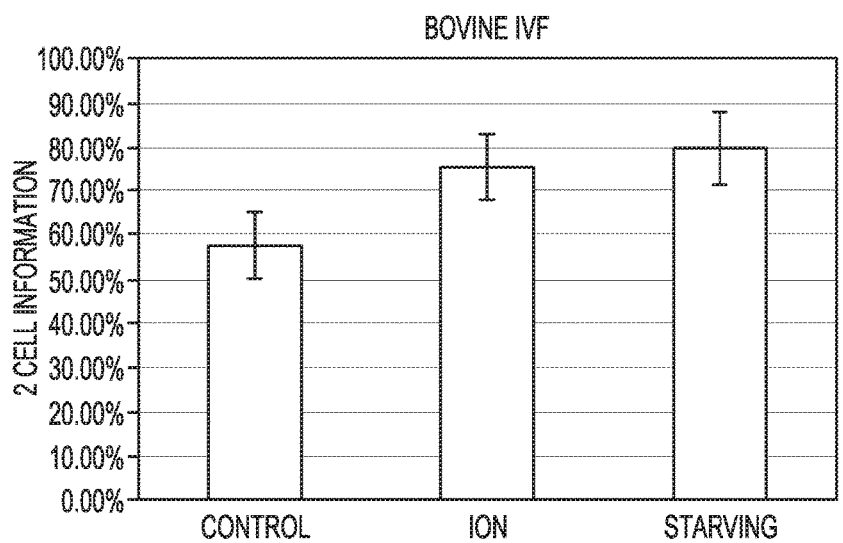
FIGS. 14A-14D. Bovine IVF is improved when sperm are treated with metabolically-enhanced media. Frozen bovine sperm were thawed and incubated in control IVF media or in metabolically-enhanced IVF media (MEM). In vitro fertilization was conducted with eggs from ovaries obtained from slaughter houses and matured in vitro. Notice that different to mouse eggs, the quality of these eggs is not homogeneous and may influence in vitro fertilization from the egg side. A. IVF was assessed by counting the percentage of oocytes that reach the two-cell embryo stage. B. Development was assessed by evaluating the percentage of 2-cell embryos that reach blastocyst stage. C. 2 blastocysts were obtained with control IVF. D. 4 blastocysts were obtained using MEM-treated sperm.
Figure 14B:
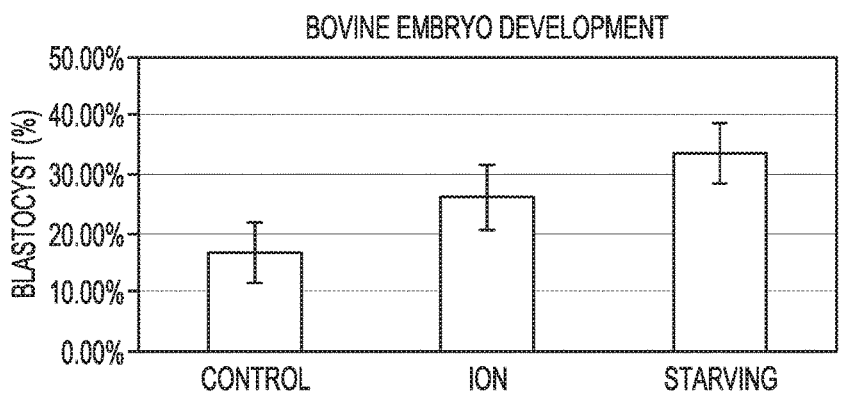
Figure 14C:
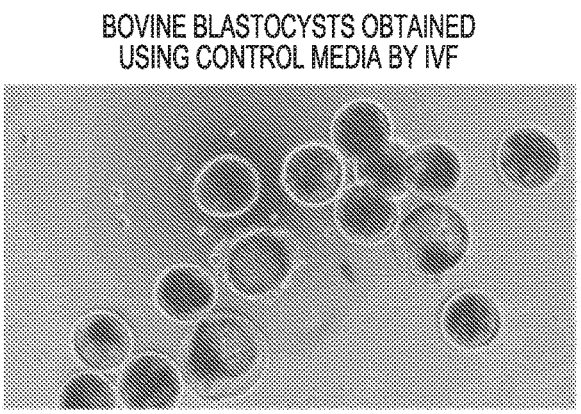
Figure 14D:
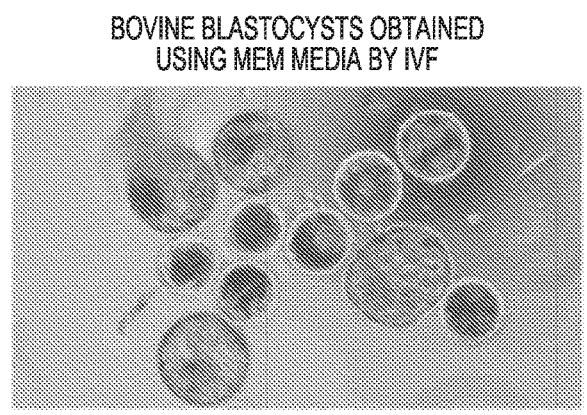

Media requirements for sperm in ART approaches vary greatly among species and have been developed for each sperm type essentially by trial and error. However, in all cases sperm need to efficiently synthesize ATP. To investigate the extent by which metabolic regulation can be used in other animal models, bovine sperm was used to conduct IVF, ICSI and embryo development experiments. These experiments were obtained using frozen sperm and in vitro matured embryo. IVF in bovines is well-established and the efficiency of the method is around 60%. Control and metabolically modified sperm performed similarly in IVF (FIG. 14 A); however, an increased percentage of blastocysts were obtained with the metabolically treated sperm (FIG. 14B). Blastocysts from one of the experiments are shown (FIGS. 14C and 14D).

Figure 15A:
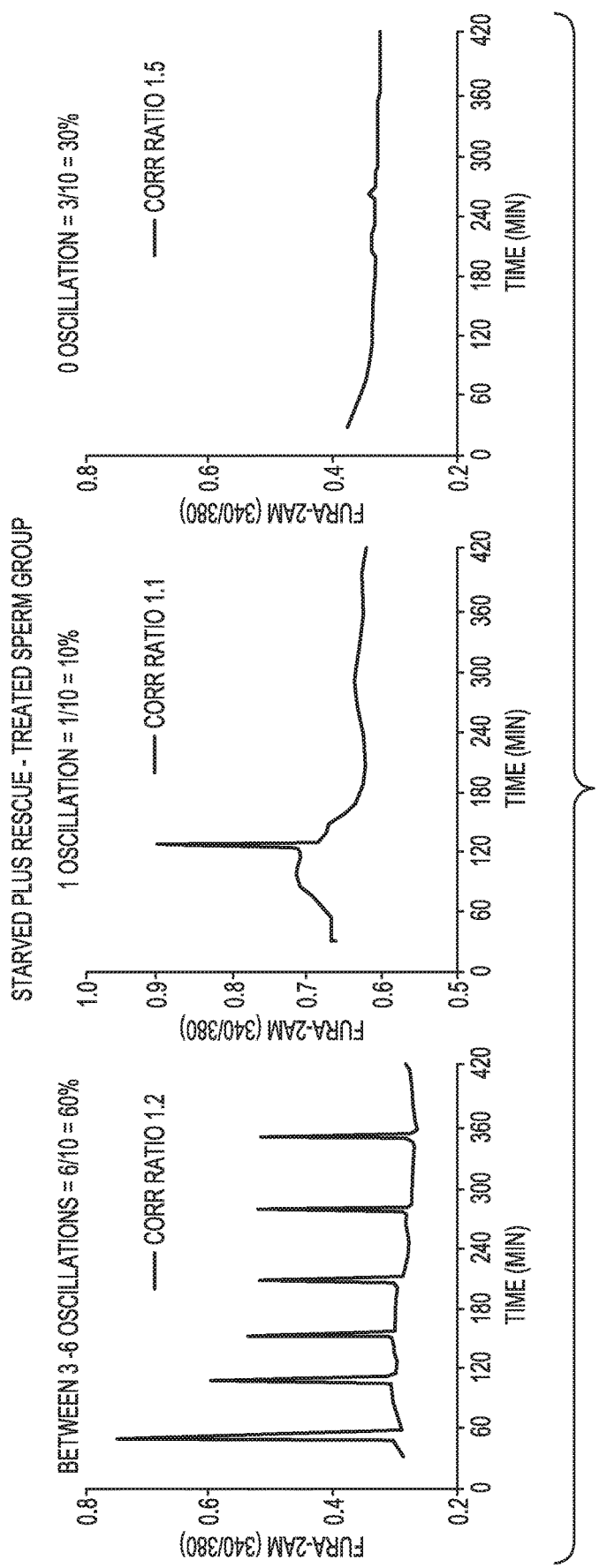
FIGS. 15A-15B. Calcium oscillations elicited by intracellular-sperm injection (ICSI) are enhanced when sperm are treated with metabolically-enhanced media. Frozen bovine sperm were thawed and incubated in control IVF media or in metabolically-enhanced IVF media (starved plus rescue). ICSI was conducted using eggs from ovaries obtained from slaughter houses and matured in vitro. Oocytes were previously loaded with the calcium dye Fura 2. Oscillations were measured for six hours after sperm injection. A. Calcium oscillations after injections of starved plus rescue-treated bovine sperm. B. Calcium oscillations after injection of control bovine sperm.
Figure 15B:
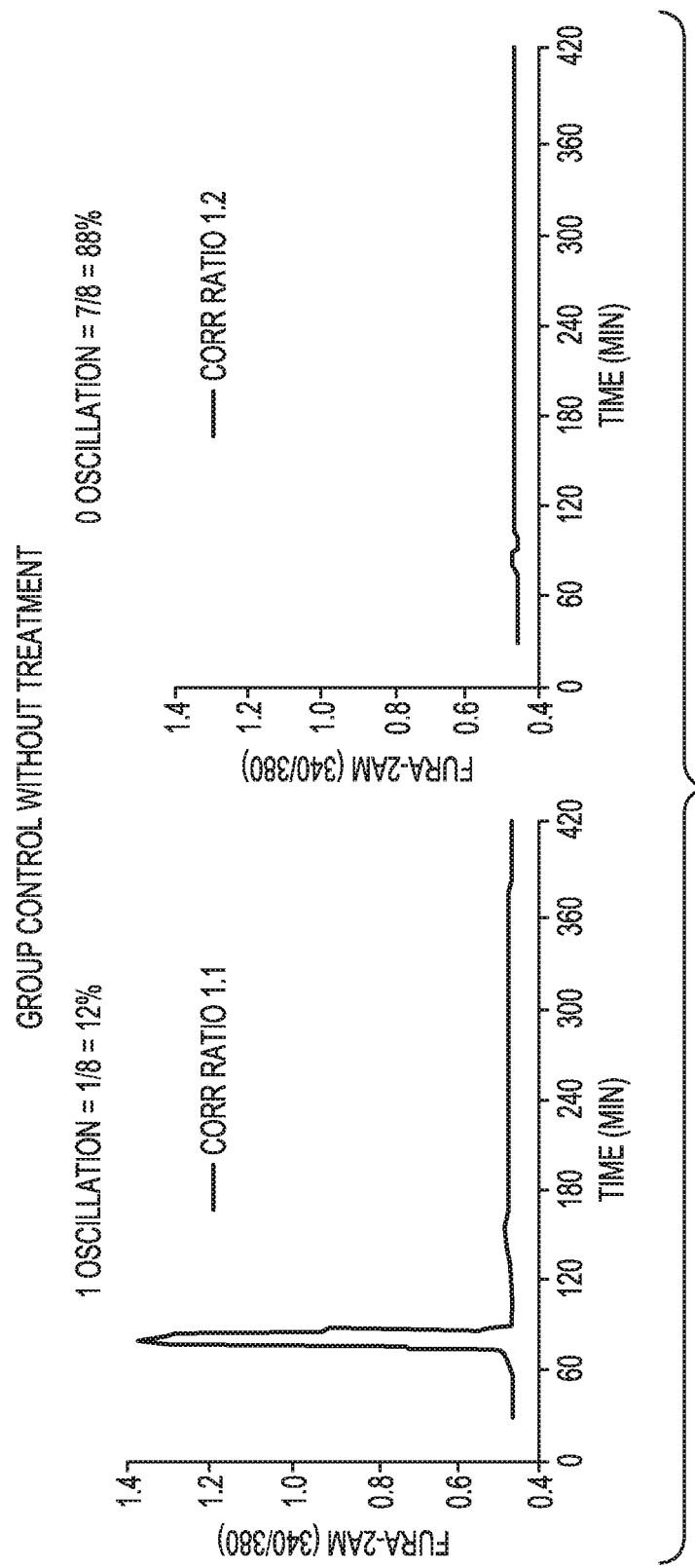
Figure 16:
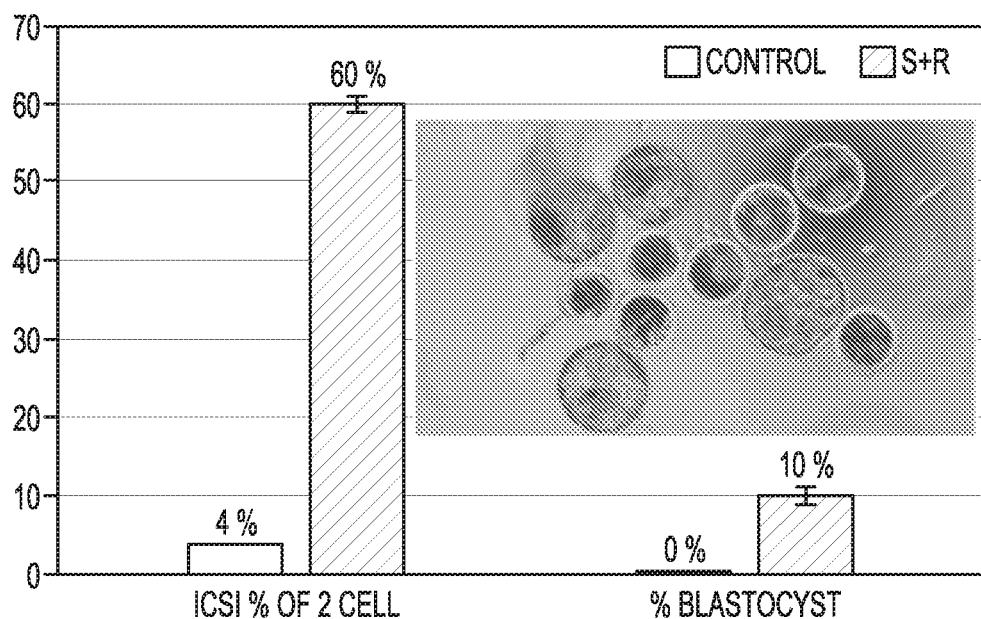
FIG. 16. Starved and rescue protocol improves two-cell and blastocyst development when bovine sperm are used in ICSI. Frozen bovine sperm were thawed and incubated in control IVF media or following the starved and rescue protocol. ICSI was conducted using eggs from ovaries obtained from slaughter houses and matured in vitro. A. IVF was assessed by counting the percentage of oocytes that reach two-cell embryo stages. B. Development was assessed by evaluating the percentage of 2-cell embryos that reach blastocyst stage.

Although as said, IVF methods are well-established in bovine, intracellular sperm injection (ICSI) is not effective using bovine sperm. This is due to deficiencies in the ability of sperm to induce Ca2+ oscillations. Therefore, the only method available to do ICSI with bovine sperm is by treating embryos with pharmacological reagents such as Ca2+ ionophores which activates the egg. Notice that one main difference on the Ca2+ ionophore treatment herein is that in the instant case, only the sperm are transiently exposed to this pharmacological reagent and that the reagent is washed out before the sperm become in contact with the egg. In an unexpected result, bovine sperm incubated in starved media and then exposed to nutrients acquire the ability to induce calcium oscillations in bovine eggs after injection by ICSI (FIG. 15 A) in significantly more number of injected eggs than controls (FIG. 15B). Moreover, this method also increased significantly the percentage of two cell embryos (FIG. 16 A) and 2 blastocysts were obtained using this treatment (FIG. 16B). Although in comparison with mouse sperm data the percentage of blastocysts appear low, it is important to highlight that this is the first time that blastocyst are obtained using ICSI without exposing the embryo to pharmacological reagents.

The methods described herein find use in IVF, ICSI and artificial insemination in humans and other mammals animals. However, each species has specific difficulties. For example, in humans, artificial insemination is not used frequently despite being the less invasive and costly method because the success rate is limited. The methods described herein improve the outcome of intrauterine insemination as well as for vaginal insemination.

BIBLIOGRAPHY

1. Tateno H, et al. Ca2+ ionophore A23187 can make mouse spermatozoa capable of fertilizing in vitro without activation of cAMP-dependent phosphorylation pathways. Proc Natl Acad Sci USA 110, 18543-18548 (2013).
2. Steptoe P C, Edwards R G. Birth after the reimplantation of a human embryo. Lancet 2, 366 (1978).
3. Chang M C. Fertilization of rabbit ova in vitro. Nature 184(Suppl 7), 466-467 (1959).
4. Chang M C. Fertilizing capacity of spermatozoa deposited into the fallopian tubes. Nature 168, 697-698 (1951).
5. Austin CR. Observations on the penetration of the sperm in the mammalian egg. Aust J Sci Res (B) 4, 581-596 (1951).
6. Yanagimachi R. Mammalian fertilization. In: The Physiology of Reproduction (ed^(eds Knobil E, Neill J D). Raven Press, Ltd. (1994).
7. Visconti P E, Krapf D, de la Vega-Beltran J L, Acevedo J J, Darszon A. Ion channels, phosphorylation and mammalian sperm capacitation. Asian J Androl 13, 395-405 (2011).
8. Harrison R A. Rapid PKA-catalysed phosphorylation of boar sperm proteins induced by the capacitating agent bicarbonate. Mol Reprod Dev 67, 337-352 (2004).
9. Krapf D, et al. Inhibition of Ser/Thr phosphatases induces capacitation-associated signaling in the presence of Src kinase inhibitors. J Biol Chem 285, 7977-7985 (2010).
10. Davis B K, Byrne R, Bedigian K. Studies on the mechanism of capacitation: albumin-mediated changes in plasma membrane lipids during in vitro incubation of rat sperm cells. Proc Natl Acad Sci USA 77, 1546-1550 (1980).
11. Cross N L. Effect of cholesterol and other sterols on human sperm acrosomal responsiveness. Mol Reprod Dev 45, 212-217 (1996).
12. Gadella B M, Harrison R A. The capacitating agent bicarbonate induces protein kinase A-dependent changes in phospholipid transbilayer behavior in the sperm plasma membrane. Development 127, 2407-2420 (2000).
13. Zeng Y, Oberdorf J A, Florman H M. pH regulation in mouse sperm: identification of Na(+)-, Cl(−)-, and HCO3(−)-dependent and arylaminobenzoate-dependent regulatory mechanisms and characterization of their roles in sperm capacitation. Dev Biol 173, 510-520 (1996).
14. Zeng Y, Clark E N, Florman H M. Sperm membrane potential: hyperpolarization during capacitation regulates zona pellucida-dependent acrosomal secretion. Dev Biol 171, 554-563 (1995).
15. Escoffier J, Krapf D, Navarrete F, Darszon A, Visconti P E. Flow cytometry analysis reveals a decrease in intracellular sodium during sperm capacitation. J Cell Sci 125, 473-485 (2012).
16. de La Vega-Beltran J L, et al. Mouse sperm membrane potential hyperpolarization is necessary and sufficient to prepare sperm for the acrosome reaction. J Biol Chem In Press, (2012).
17. Ruknudin A, Silver I A. Ca2+ uptake during capacitation of mouse spermatozoa and the effect of an anion transport inhibitor on Ca2+ uptake. Mol Reprod Dev 26, 63-68 (1990).

18. Visconti P E, Bailey J L, Moore G D, Pan D, Olds-Clarke P, Kopf G S. Capacitation of mouse spermatozoa. I. Correlation between the capacitation state and protein tyrosine phosphorylation. Development 121, 1129-1137 (1995).
19. Ren D, et al. A sperm ion channel required for sperm motility and male fertility. Nature 413, 603-609 (2001).
20. Xie F, et al. Soluble adenylyl cyclase (sAC) is indispensable for sperm function and fertilization. Dev Biol 296, 353-362 (2006).
21. Sachan D S, Hoppel C L. Carnitine biosynthesis. Hydroxylation of N6-trimethyl-lysine to 3-hydroxy-N6-trimethyl-lysine. Biochem J 188, 529-534 (1980).
22. Esposito G, et al. Mice deficient for soluble adenylyl cyclase are infertile because of a severe sperm-motility defect. Proc Natl Acad Sci USA 101, 2993-2998 (2004).
23. Escoffier J, Navarrete F, Haddad D, Santi C M, Darszon A, Visconti PE. Flow Cytometry Analysis Reveals That Only a Subpopulation of Mouse Sperm Undergoes Hyperpolarization During Capacitation. Biol Reprod, (2015).
24. Zeng X H, Yang C, Kim S T, Lingle C J, Xia X M. Deletion of the Slo3 gene abolishes alkalization-activated K+ current in mouse spermatozoa. Proc Natl Acad Sci USA 108, 5879-5884 (2011).
25. Zeng X H, Yang C, Xia X M, Liu M, Lingle C J. SLO3 auxiliary subunit LRRC52 controls gating of sperm KSPER currents and is critical for normal fertility. Proc Natl Acad Sci USA 112, 2599-2604 (2015).
26. Okunade G W, et al. Targeted ablation of plasma membrane Ca2+-ATPase (PMCA) 1 and 4 indicates a major housekeeping function for PMCA1 and a critical role in hyperactivated sperm motility and male fertility for PMCA4. J Biol Chem 279, 33742-33750 (2004).
27. Kawai Y, Hata T, Suzuki O, Matsuda J. The relationship between sperm morphology and in vitro fertilization ability in mice. J Reprod Dev 52, 561-568 (2006).
28. Nishizono H, Shioda M, Takeo T, Irie T, Nakagata N. Decrease of fertilizing ability of mouse spermatozoa after freezing and thawing is related to cellular injury. Biol Reprod 71, 973-978 (2004).
29. Songsasen N, Leibo S P. Cryopreservation of mouse spermatozoa. II. Relationship between survival after cryopreservation and osmotic tolerance of spermatozoa from three strains of mice. Cryobiology 35, 255-269 (1997).
30. Sztein J M, Farley J S, Mobraaten L E. In vitro fertilization with cryopreserved inbred mouse sperm. Biol Reprod 63, 1774-1780 (2000).
31. Liu L, Nutter L M, Law N, McKerlie C. Sperm freezing and in vitro fertilization in three substrains of C57BL/6 mice. J Am Assoc Lab Anim Sci 48, 39-43 (2009).
32. Nolan M A, Babcock D F, Wennemuth G, Brown W, Burton K A, McKnight G S. Sperm-specific protein kinase A catalytic subunit Calpha2 orchestrates cAMP signaling for male fertility. Proc Natl Acad Sci USA 101, 13483-13488 (2004).
33. Bin Ali R, et al. Improved pregnancy and birth rates with routine application of nonsurgical embryo transfer. Transgenic Res 23, 691-695 (2014).
34. Wennemuth G, Babcock D F, Hille B. Calcium clearance mechanisms of mouse sperm. J Gen Physiol 122, 115-128 (2003).
35. Prasad V, Okunade G W, Miller M L, Shull G E. Phenotypes of SERCA and PMCA knockout mice. Biochem Biophys Res Commun 322, 1192-1203 (2004).
36. Visconti P E. Understanding the molecular basis of sperm capacitation through kinase design. Proc Natl Acad Sci USA 106, 667-668 (2009).
37. Wennemuth G, Carlson A E, Harper A J, Babcock D F. Bicarbonate actions on flagellar and Ca2+-channel responses: initial events in sperm activation. Development 130, 1317-1326 (2003).
38. Carlson A E, Quill T A, Westenbroek R E, Schuh S M, Hille B, Babcock D F. Identical phenotypes of CatSper1 and CatSper2 null sperm. J Biol Chem 280, 32238-32244 (2005).
39. Hess K C, et al. The "soluble" adenylyl cyclase in sperm mediates multiple signaling events required for fertilization. Dev Cell 9, 249-259 (2005).
40. Yanagimachi R. The movement of golden hamster spermatozoa before and after capacitation. J Reprod Fertil 23, 193-196 (1970).
41. Burkman L J. Characterization of Hyperactivated Motility by Human-Spermatozoa during Capacitation—Comparison of Fertile and Oligozoospermic Sperm Populations. Arch Andrology 13, 153-165 (1984).
42. Suarez S S, Osman R A. Initiation of hyperactivated flagellar bending in mouse sperm within the female reproductive tract. Biol Reprod 36, 1191-1198 (1987).
43. Carlson A E, et al. CatSper1 required for evoked Ca2+ entry and control of flagellar function in sperm. Proc Natl Acad Sci USA 100, 14864-14868 (2003).
44. Danshina P V, et al. Phosphoglycerate kinase 2 (PGK2) is essential for sperm function and male fertility in mice. Biol Reprod 82, 136-145 (2010).
45. Miki K, et al. Glyceraldehyde 3-phosphate dehydrogenase-S, a sperm-specific glycolytic enzyme, is required for sperm motility and male fertility. Proc Natl Acad Sci USA 101, 16501-16506 (2004).
46. Yanagimachi R. Requirement of Extracellular Calcium-Ions for Various Stages of Fertilization and Fertilization-Related Phenomena in the Hamster. Gamete Research 5, 323-344 (1982).
47. Cooper T G. The Onset and Maintenance of Hyperactivated Motility of Spermatozoa from the Mouse. Gamete Research 9, 55-74 (1984).
48. Yanagimachi R, Usui N. Calcium dependence of the acrosome reaction and activation of guinea pig spermatozoa. Exp Cell Res 89, 161-174 (1974).
49. Ahmad K, Bracho G E, Wolf D P, Tash J S. Regulation of human sperm motility and hyperactivation components by calcium, calmodulin, and protein phosphatases. Arch Androl 35, 187-208. (1995).
50. Suarez S S, Vincenti L, Ceglia M W. Hyperactivated motility induced in mouse sperm by calcium ionophore A23187 is reversible. J Exp Zool 244, 331-336 (1987).
51. Visconti P E, et al. Roles of bicarbonate, cAMP, and protein tyrosine phosphorylation on capacitation and the spontaneous acrosome reaction of hamster sperm. Biol Reprod 61, 76-84 (1999).
52. Tateno H, Mikamo K. A Chromosomal Method to Distinguish between X-Bearing and Y-Bearing Spermatozoa of the Bull in Zona-Free Hamster Ova. Journal of Reproduction and Fertility 81, 119-125 (1987).
53. Schuh K, et al. Plasma membrane Ca2+ ATPase 4 is required for sperm motility and male fertility. J Biol Chem 279, 28220-28226 (2004).
54. Sharlip I D, et al. Best practice policies for male infertility. Fertil Steril 77, 873-882 (2002).
55. Martinez G, Daniels K, Chandra A. Fertility of men and women aged 15-44 years in the United States: National Survey of Family Growth, 2006-2010. Natl Health Stat Report, 1-28 (2012).

56. Santi C M, et al. The SLO3 sperm-specific potassium channel plays a vital role in male fertility. FEBS Lett 584, 1041-1046 (2010).
57. Coy P, Garcia-Vazquez F A, Visconti P E, Aviles M. Roles of the oviduct in mammalian fertilization. Reproduction 144, 649-660 (2012).
58. Tokuhiro K, Ikawa M, Benham A M, Okabe M. Protein disulfide isomerase homolog PDILT is required for quality control of sperm membrane protein ADAM3 and male fertility [corrected]. Proc Natl Acad Sci USA 109, 3850-3855 (2012).
59. Hinrichs K. Assisted reproduction techniques in the horse. Reproduction, Fertility and Development 25, 80-93 (2013).
60. Hinrichs K, Love C C, Brinsko S P, Choi Y H, Varner D D. In vitro fertilization of in vitro-matured equine oocytes: effect of maturation medium, duration of maturation, and sperm calcium ionophore treatment, and comparison with rates of fertilization in vivo after oviductal transfer. Biol Reprod 67, 256-262 (2002).
61. Choi Y H, Okada Y, Hochi S, Braun J, Sato K, Oguri N. In vitro fertilization rate of horse oocytes with partially removed zonae. Theriogenology 42, 795-802 (1994).
62. Thompson P. HFEA response to 'A plea for caution and more research in the "experimental" use of ionophores in ICSI'. Reprod Biomed Online 31, 829-830 (2015).
63. Laemmli U K. Cleavage of structural proteins during the assembly of the head of bacteriophage T4. Nature 227, 680-685 (1970).
64. Goodson S G, Zhang Z, Tsuruta J K, Wang W, O'Brien D A. Classification of mouse sperm motility patterns using an automated multiclass support vector machines model. Biol Reprod 84, 1207-1215 (2011).
65. Green M, Bass S, Spear B. A device for the simple and rapid transcervical transfer of mouse embryos eliminates the need for surgery and potential post-operative complications. Biotechniques 47, 919-924 (2009).
Bin Ali R, van der Ahe F, Braumuller T M, Pritchard C, Krimpenfort P, Berns A, Huijbers I J. 2014. Improved pregnancy and birth rates with routine application of non-surgical embryo transfer. Transgenic Res 23(4):691-695.
Sharlip I D, Jarow J P, Belker A M, Lipshultz L I, Sigman M, Thomas A J, Schlegel P N, Howards S S, Nehra A, Damewood M D, Overstreet J W, Sadovsky R. 2002. Best practice policies for male infertility. Fertil Steril 77(5): 873-882.

The invention is described with reference to various specific and preferred embodiments and techniques. However, it should be understood that many variations and modifications may be made while remaining within its scope. All referenced publications, patents and patent documents are intended to be incorporated by reference, as though individually incorporated by reference.

What is claimed is:

1. A method to increase Artificial Insemination pregnancy rates comprising
    a) isolating biological fluid comprising sperm;
    b) removing energy nutrients from said biological fluid in a);
    c) placing said sperm of a) and/or b) in a media absent energy nutrients including glucose and pyruvate for a period of time sufficient for the sperm to lose progressive motility;
    d) adding an energy nutrient to said media and sperm of c), wherein said energy nutrient is a glycolytic substrate or a Krebs cycle substrate or a combination thereof; and
    e) using said sperm from c) or d) for intrauterine or vaginal insemination so as to increase Artificial Insemination pregnancy rates as compared to a method where sperm cells have not under gone energy nutrient starvation.

2. The method of claim 1, wherein the energy nutrient added to said media in step d) is glucose, fructose, pyruvate, lactate, citrate or a combination thereof.

3. The method of claim 1, wherein the sperm is from a vertebrate.

4. The method of claim 1, wherein the sperm cells are further exposed to an ionophore.

5. The method of claim 1, wherein the ionophore is a calcium.

6. The method of claim 1, wherein in step c) glycolytic and Krebs cycle metabolites are not present.

7. The method of claim 1, wherein in step c) glucose, pyruvate and lactate are not present.

* * * * *